United States Patent
Yilmaz et al.

(10) Patent No.: US 9,334,170 B2
(45) Date of Patent: May 10, 2016

(54) PROCESS FOR THE PRODUCTION OF A CORE/SHELL ZEOLITIC MATERIAL HAVING A CHA FRAMEWORK STRUCTURE

(75) Inventors: Bilge Yilmaz, New York, NY (US); Ulrich Müller, Neustadt (DE); Feng-Shou Xiao, Changchun (CN); Takashi Tatsumi, Kawasaki (JP); Dirk de Vos, Holsbeek (BE); Xinhe Bao, Dalian (CN); Weiping Zhang, Dalian (CN); Hermann Gies, Sprockhövel (DE); Hiroyuki Imai, Tokyo (JP); Bart Tijsebaert, Sint-Andries (BE); Limin Ren, Changchun (CN); Chengguan Yang, Changchun (CN)

(73) Assignees: BASF SE, Ludwigshafen (DE); Tokyo Institute of Technology, Tokyo (JP)

( * ) Notice: Subject to any disclaimer, the term of this patent is extended or adjusted under 35 U.S.C. 154(b) by 909 days.

(21) Appl. No.: 13/616,834

(22) Filed: Sep. 14, 2012

(65) Prior Publication Data
US 2013/0101503 A1    Apr. 25, 2013

(30) Foreign Application Priority Data

Sep. 16, 2011   (WO) ................ PCT/CN2011/079746

(51) Int. Cl.
*C01B 39/00*    (2006.01)
*B01J 29/85*    (2006.01)
(Continued)

(52) U.S. Cl.
CPC ............... *C01B 39/00* (2013.01); *B01J 29/005* (2013.01); *B01J 29/7015* (2013.01); *B01J 29/83* (2013.01);
(Continued)

(58) Field of Classification Search
CPC ........ C01B 39/48; C01B 39/54; C01B 39/00; C01B 39/08; B01J 2229/62; B01J 37/0221; B01J 35/023; B01J 35/1023; B01J 35/1066; B01J 29/005; B01J 29/83; B01J 29/84; B01J 29/85; B01J 35/1019; B01J 29/7015; C07C 1/20; C07C 11/05; C07C 2529/85
See application file for complete search history.

(56) References Cited

U.S. PATENT DOCUMENTS 5,888,921 A    3/1999   Tsang et al.
6,974,889 B1  12/2005  Verduijn et al.
(Continued)

FOREIGN PATENT DOCUMENTS

| CN | 101314135 | 12/2008 |
| GB | 2451864 | 2/2009 |
| WO | WO 2008/049537 | 5/2008 |

OTHER PUBLICATIONS

Marchese et al, ALPO-34 and SAPO-34 synthesized by using morpholine as templating agent . . . , Microporous and Mesoporous Materails, vol. 30, No. 1, (Aug. 1999) pp. 145-153.*

(Continued)

*Primary Examiner* — David M Brunsman
(74) *Attorney, Agent, or Firm* — Servilla Whitney LLC

(57) ABSTRACT

The present invention relates to a process for the preparation of a zeolitic material having a CHA framework structure, said zeolitic material comprising zeolite crystals having a core-shell structure, wherein said process comprises the steps of
(1) providing a mixture comprising one or more sources for $Z_2O_5$, one or more sources for $X_2O_3$, optionally one or more structure directing agents, and seed crystals having a CHA framework structure, wherein the CHA framework structure of the seed crystals comprises $YO_2$, $X_2O_3$, and optionally $Z_2O_5$, and wherein the seed crystals have a diameter of 450 nm or greater;
(2) crystallizing the mixture provided in (1) to afford zeolite crystals comprising a core of seed crystal provided in step (1) and a shell crystallized on the seed crystal;
wherein Z is a pentavalent element, Y is a tetravalent element, and X is a trivalent element.

32 Claims, 8 Drawing Sheets

(51) Int. Cl.

| | |
|---|---|
| *B01J 37/02* | (2006.01) |
| *B01J 29/00* | (2006.01) |
| *B01J 29/84* | (2006.01) |
| *B01J 29/83* | (2006.01) |
| *C01B 39/54* | (2006.01) |
| *C01B 37/08* | (2006.01) |
| *C01B 39/48* | (2006.01) |
| *B01J 29/70* | (2006.01) |
| *B01J 35/00* | (2006.01) |
| *B01J 35/02* | (2006.01) |
| *B01J 35/10* | (2006.01) |
| *C07C 1/20* | (2006.01) |
| *C10G 11/18* | (2006.01) |
| *C10G 3/00* | (2006.01) |
| *B01D 53/02* | (2006.01) |
| *B01D 53/94* | (2006.01) |

(52) U.S. Cl.
CPC ......... *B01J 29/84* (2013.01); *B01J 29/85* (2013.01); *B01J 35/002* (2013.01); *B01J 35/023* (2013.01); *B01J 35/1019* (2013.01); *B01J 35/1023* (2013.01); *B01J 35/1066* (2013.01); *B01J 37/02* (2013.01); *B01J 37/023* (2013.01); *B01J 37/0221* (2013.01); *C01B 37/08* (2013.01); *C01B 39/48* (2013.01); *C01B 39/54* (2013.01); *C07C 1/20* (2013.01); *C10G 3/49* (2013.01); *C10G 11/18* (2013.01); *B01D 53/02* (2013.01); *B01D 53/9418* (2013.01); *B01D 2255/2025* (2013.01); *B01D 2255/2092* (2013.01); *B01D 2255/2094* (2013.01); *B01D 2255/20707* (2013.01); *B01D 2255/20715* (2013.01); *B01D 2255/50* (2013.01); *B01J 2229/62* (2013.01); *C01P 2002/72* (2013.01); *C01P 2004/03* (2013.01); *C01P 2006/12* (2013.01); *C07C 2529/85* (2013.01); *Y02P 20/52* (2015.11); *Y02P 30/20* (2015.11)

(56) References Cited

U.S. PATENT DOCUMENTS 7,067,108 B2    6/2006   Mertens et al.
7,442,365 B1 *  10/2008  Jacobsen ............... B01J 29/06
                                              423/305

OTHER PUBLICATIONS

Virta, "Mineral Resource of the Month: Zeolites", Earth, USGS, (Nov. 2014).*
PCT International Search Report in PCT/IB2012/054800, mailed Feb. 28, 2013, 4 pgs.
Extended European Search Report in EP12832035, dated Jun. 1, 2015, 10 pages.
Bouizi, Younes, et al., Bi-phase MOR/MFI-type zeolite core-shell composite, *Microporous and Mesoporous Materials* vol. 91 2006, 70-77.
Kahn, Easir A., et al., Preparation of metal oxide/zeolite core-shell nanostructures, *Microporous and Mesoporous Materials* vol. 118 2009, 210-217.

* cited by examiner

A

B

A 1 h

B 2 h

C 9 h

A 1 h

B 2 h

C 9 h

PROCESS FOR THE PRODUCTION OF A CORE/SHELL ZEOLITIC MATERIAL HAVING A CHA FRAMEWORK STRUCTURE

CROSS-REFERENCE TO RELATED APPLICATIONS

This application claims priority under 35 USC §365 (c) to PCT/CN2011/079746, filed Sep. 16, 2011, the contents of which is specifically incorporated by reference herein in its entirety.

TECHNICAL FIELD

The present invention relates to a zeolitic material having a CHA framework structure and to a method for its production, wherein the crystals of the zeolitic material display a core/shell structure, as well as to the use of a core/shell zeolitic material having a CHA framework structure.

BACKGROUND OF THE INVENTION

Molecular sieves are classified by the Structure Commission of the International Zeolite Association according to the rules of the IUPAC Commission on Zeolite Nomenclature. According to this classification, framework-type zeolites and other crystalline microporous molecular sieves, for which a structure has been established, are assigned a three letter code and are described in the Atlas of Zeolite Framework Types, 5th edition, Elsevier, London, England (2001).

Among said zeolitic materials, Chabazite is a well studied example, wherein it is the classical representative of the class of zeolitic materials having a CHA framework structure. Besides aluminosilicates such as Chabazite, the class of zeolitic materials having a CHA framework structure comprises a large number of compounds further comprising phosphorous in the framework structure are known which are accordingly referred to as silicoaluminophosphates (SAPO). In addition to said compounds, further molecular sieves of the CHA structure type are known which contain aluminum and phosphorous in their framework, yet contain little or no silica, and are accordingly referred to as aluminophosphates (APO). Zeolitic materials belonging to the class of molecular sieves having the CHA-type framework structure are employed in a variety of applications, and in particular serve as heterogeneous catalysts in a wide range of reactions such as in methanol to olefin catalysis and selective catalytic reduction of nitrogen oxides $NO_x$ to name some two of the most important applications. Zeolitic materials of the CHA framework type are characterized by three-dimensional 8-membered-ring (8MR) pore/channel systems containing double-six-rings (D6R) and cages.

U.S. Pat. No. 7,067,108 B2 discloses zeolites of Chabazite framework type. These zeolites are prepared by employing a specific seeding material, namely a crystalline material having a framework type other than Chabazite framework type, such as AEI type, LEV type, or OFF type.

U.S. Pat. No. 6,974,889 B1 on the other hand discloses a process for the manufacture of a crystalline molecular sieve, such as zeolites of structure type CHA or LEV, containing phosphorus in its framework, wherein a colloidal crystalline molecular sieve is used as seed material. In particular, said document teaches the use of seed crystals having the structure type LEV, OFF, or CHA, wherein said seed crystals should be as small as possible for controlling the particle size of the product as well as for accelerating its formation. Specifically, the synthesis of SAPO-34 is disclosed in said document using colloidal solutions of Chabazite crystals, of which the XRD would indicate a uniform particle size of 100×400 nm, and wherein the product is crystallized for a period of 60 hours.

Although considerable efforts have been made with respect to the synthetic methodologies for obtaining zeolitic materials having the CHA framework structure, there remains the need for finding novel preparation methods which are yet more efficient in providing high quality materials at a lower cost. This is a particularly challenging objective, in particular in view of the widespread use of said materials in mass-applications such as in the treatment of automotive exhaust gas and the like. Furthermore, the need is also given for the preparation of novel zeolitic materials having the CHA framework structure displaying new characteristics for use in known and future applications, in particular in the increasingly important field of catalysis.

SUMMARY OF THE INVENTION

The present invention relates to a novel synthetic methodology for the production of novel zeolitic materials having the CHA framework structure which display unprecedented physical and chemical properties. In this respect, it has surprisingly been found that the use of specific seeding materials in the preparation of a zeolitic material having a CHA framework structure affords novel zeolite crystals having a core-shell structure displaying highly unexpected properties, in particular with respect to their use in catalytic applications. Furthermore, it has surprisingly been found that through the use of said specific seeding materials a zeolitic material having a CHA framework structure may be obtained in a very short period of time, thus greatly improving the energy- and cost-efficiency of the production process.

DESCRIPTION OF THE DRAWINGS

FIG. 1B shows the image at higher magnification as compared to FIG. 1A.

Figure 7:
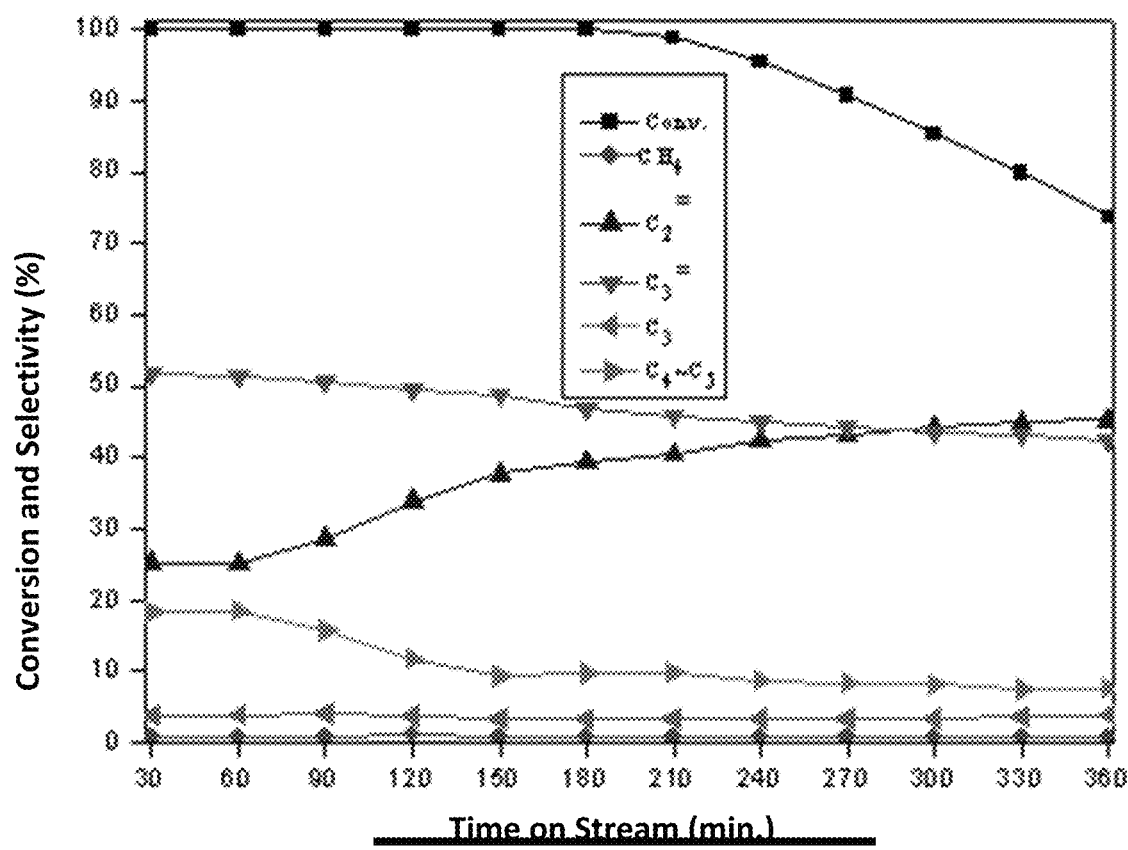
Figure 8:
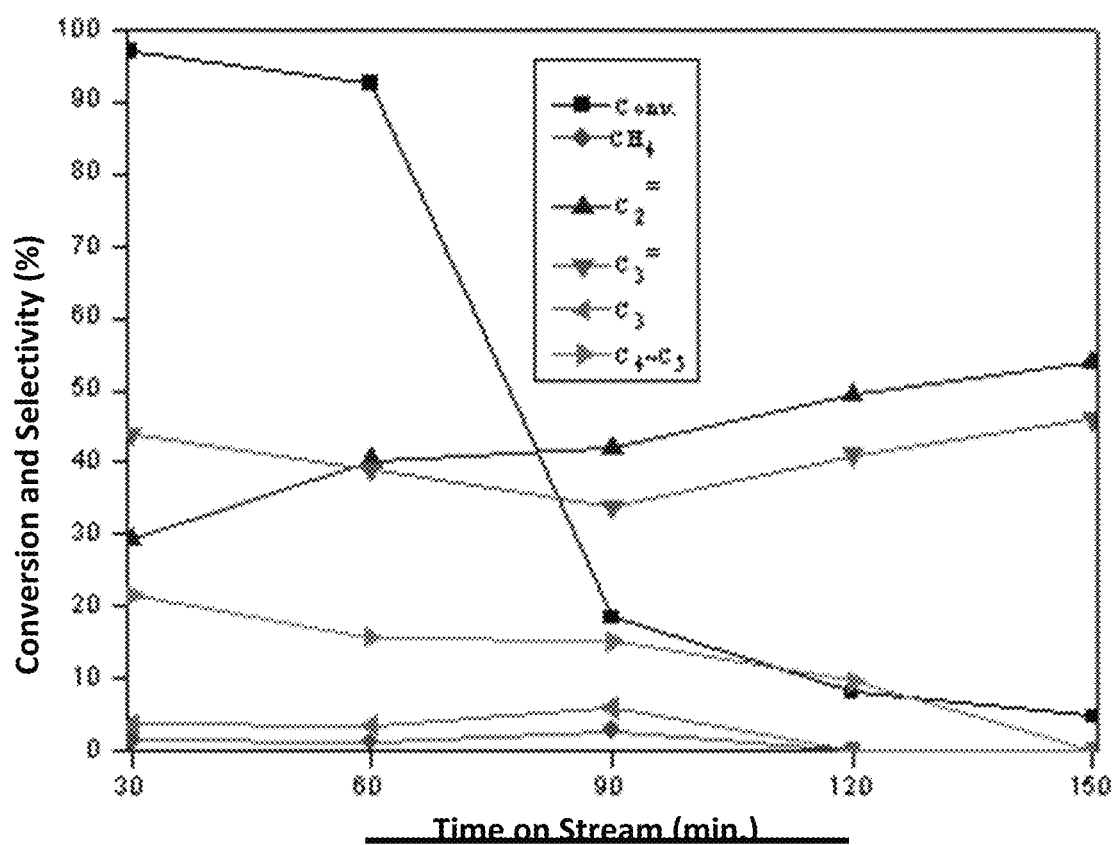

FIGS. 7 and 8 display the results obtained from methanol to olefin (MTO) testing performed in Example 3, wherein the conversion and selectivity are plotted along the ordinate in %, and the time on stream is plotted along the abscissa, respectively. In the Figure, the symbol "■" represents the conversion grade, "♦" represents the selectivity towards methane, "▲" represents the selectivity towards $C_2$-olefin, "▼" represents the selectivity towards $C_3$-olefin, "◄" represents the selectivity towards $C_3$-alkane, and "►" represents the selectivity towards $C_4$ and $C_5$-alkane.

DETAILED DESCRIPTION

Thus the present invention relates to a process for the preparation of a zeolitic material having a CHA framework structure, said zeolitic material comprising zeolite crystals having a core-shell structure, wherein said process comprises the steps of
(1) providing a mixture comprising one or more sources for $Z_2O_5$, one or more sources for $X_2O_3$, optionally one or more structure directing agents, and seed crystals having a CHA framework structure, wherein the CHA framework structure of the seed crystals comprises $YO_2$, $X_2O_3$, and optionally $Z_2O_5$, and wherein the seed crystals have a diameter of 450 nm or greater;
(2) crystallizing the mixture provided in (1) to afford zeolite crystals comprising a core of seed crystal provided in step (1) and a shell crystallized on the seed crystal; wherein Z is a pentavalent element, Y is a tetravalent element, and X is a trivalent element, and
wherein preferably one or more sources for $YO_2$ are further provided in step (1).

Accordingly, it has surprisingly been found that in a process for the preparation of a zeolitic material having a CHA framework structure, by using crystal seeds of a certain size and, in particular, of which the diameter is 450 nm or greater, novel zeolitic materials having a core-shell structure displaying highly unexpected properties may be obtained, in particular with respect to their use in catalytic applications. Furthermore, it has quite unexpectedly been found that the crystallization period in a process for the preparation of a zeolitic material having a CHA framework structure may be greatly reduced using seed crystals of a certain size as defined in the present application. These are highly unexpected findings especially in view of the fact that generally, the use of seed crystals in procedures for the synthesis of zeolites having a CHA framework structure is exclusively taught as a means for enabling and/or enhancing nucleation, wherein in particular the use of a seeding material having dimensions which are as small as possible is taught in view of increasing the number of seeds for a given wt.-% of seed crystals being used. Accordingly, the possibility of using larger seed crystals for achieving novel zeolitic materials having a core-shell structure displaying unprecedented physical and chemical properties constitutes a highly unexpected finding. In addition to this, it was highly unexpected that the use of larger seed crystals actually provides an effective means of nucleation in reaction mixtures, but even more surprisingly actually considerably increases the crystallization rate, thus allowing for the effective crystallization of zeolitic materials having a CHA framework structure after only very short periods of crystallization.

Within the meaning of the present invention the term "zeolitic material" generally refers to any zeolite containing material. According to a preferred meaning, the term zeolitic material refers to one or more zeolites. "Zeolites" as related to in the context of the present invention are crystalline compounds with well-ordered channel or cage structures containing micropores. The expression "micropore" as used in the context of the present invention corresponds to the definition given in "Pure Applied Chemistry" (1976), Vol. 45, p. 71 ff., in particular p. 79. According to this definition, micropores are pores with a pore diameter of less than 2 nm. The network of these zeolites is made of $YO_4$ and $XO_4$-tetrahedra that are bridged via shared oxygen bonds. An overview of the known structures can be found in, e.g., W. M. Meier and D. H. Olson in "Atlas of Zeolite Structure Types", Elsevier, 4th Ed., London 1996. In addition to micropores, the zeolitic materials according to the invention may also contain mesopores and/or macropores as well. According to a particularly preferred meaning of the present invention, the term "zeolite" refers to one or more aluminosilicate compounds, and the term "zeolitic material" accordingly to a material containing one or more zeolites, and more preferably to the one or more zeolites themselves.

Furthermore, in the zeolitic material which may be obtained according to the inventive process, $YO_2$, $X_2O_3$, and $Z_2O_5$ comprised therein are contained in the framework structure of the zeolitic material having a CHA framework structure as structure building elements, as opposed to non-framework elements which can be present in the pores and/or cavities formed by the framework structure and typical for zeolitic materials in general.

Within the meaning of the present invention, the term "core-shell structure" generally refers to a composition of a solid material, wherein said solid material is a particulate material, and wherein individual particles are characterized by containing at least two different types of materials which may be distinguished from one another by their composition and/or by their structure, wherein one or more materials of a certain type are contained in the interior portion of said particles, wherein the interior portion is designated by the term "core", and wherein one or more materials of a certain type which may distinguished from the one or more materials contained in the interior portion are contained in the outer portion of said particles, thus forming the surface portion thereof, and wherein the outer portion comprising the surface is designated by the term "shell".

Furthermore, within the meaning of the present invention, the term "zeolite crystal" generally refers to individual particles of a particulate zeolitic material, said individual particles having been formed by crystallization, and in particular by one or more crystallization steps. In particular, in conjunction with the term "core-shell structure" characterizing the composition of zeolite crystals according to the present invention, said zeolite crystals are characterized by containing at least two different types of zeolitic materials which may be distinguished from one another by their composition and/or by their structure, wherein one or more zeolitic materials of a certain type are contained in the interior portion or "core" of said zeolite crystals, and wherein one or more zeolitic materials of a certain type which may distinguished from the one or more zeolitic materials contained in the interior portion are contained in the outer portion of said zeolite crystals, thus forming the surface portion or "shell" thereof. In particular, a zeolite crystal having a core-shell structure within the meaning of the present invention preferably refers to a zeolite crystal comprising a core-portion containing one or more zeolitic materials and in particular one or more zeolites, onto which a shell-portion equally containing one or more zeolitic materials and in particular one or more zeolites has been directly provided, preferably by crystallization of the shell-portion onto an existing core-portion such as e.g. onto crystal seeds.

According to certain embodiments of the inventive process, the mixture provided in step (1) comprises one or more sources for $Z_2O_5$, wherein Z stands for any conceivable pentavalent element, Z standing for either one or several pentavalent elements. Preferably, $Z_2O_5$ is provided as such and/or as a compound which comprises $Z_2O_5$ as a chemical moiety and/or as a compound which (partly or entirely) is chemically transformed to $Z_2O_5$ during the inventive process. In principle, any conceivable source may be provided as the one or more sources for $Z_2O_5$, provided that in step (2) of the inventive process, a shell may be crystallized on the seed crystals provided in step (1). Preferred pentavalent elements Z according to the present invention include P, As, Sb, Bi, V, Nb, Ta, and combinations of two or more thereof. More preferably, Z stands for P, As, V, and combinations of two or more thereof, wherein even more preferably Z comprises P or As. According to particularly preferred embodiments, Z comprises P, wherein it is particularly preferred that Z stands for P.

Thus, according to one or more embodiments of the inventive process, Z provided in step (1) in the one or more sources for $Z_2O_5$ is selected from the group consisting of P, As, Sb, Bi, V, Nb, Ta, and combinations of two or more thereof, preferably from the group consisting of P, As, V, and combinations of two or more thereof, wherein more preferably Z comprises P or As, preferably P, and wherein even more preferably Z is P.

Furthermore, according to certain embodiments of the inventive process, the mixture provided in step (1) comprises one or more sources for $X_2O_3$, wherein X stands for any conceivable trivalent element, X standing for either one or several trivalent elements. Preferably, $X_2O_3$ is provided as such and/or as a compound which comprises $X_2O_3$ as a chemical moiety and/or as a compound which (partly or entirely) is chemically transformed to $X_2O_3$ during the inventive process. In principle, any conceivable source may be provided as the one or more sources for $X_2O_3$, provided that in step (2) of the inventive process, a shell may be crystallized on the seed crystals provided in step (1). Preferred trivalent elements according to the present invention include Al, B, In, and Ga, and combinations thereof. More preferably, X stands for Al or Ga. According to particularly preferred embodiments, X comprises Al, wherein it is particularly preferred that X stands for Al.

Thus, according to one or more embodiments of the inventive process, X provided in step (1) in the one or more sources for $X_2O_3$ is selected from the group consisting of Al, B, In, Ga, and combinations of two or more thereof, wherein X preferably comprises Al or Ga, wherein more preferably X comprises Al, and wherein even more preferably X is Al.

According to some embodiments of the present invention, the mixture provided in step (1) further comprises one or more sources for $YO_2$, wherein Y stands for any conceivable tetravalent element, Y standing for either one or several tetravalent elements. Preferably, $YO_2$ is provided as such and/or as a compound which comprises $YO_2$ as a chemical moiety and/or as a compound which (partly or entirely) is chemically transformed to $YO_2$ during the inventive process. Preferred tetravalent elements according to the present invention include Si, Sn, Ti, Zr, and Ge, and combinations of two or more thereof. More preferably, Y stands for Si, Ti, or Zr, or any combination of said tetravalent elements, even more preferably for Si and/or Sn. According to particularly preferred embodiments, Y comprises Si, wherein it is particularly preferred that Y stands for Si.

Therefore, according to one or more embodiments of the inventive process wherein one or more sources for $YO_2$ are further provided in step (1), it is further preferred that Y is selected from the group consisting of Si, Sn, Ti, Zr, Ge, and combinations of two or more thereof, wherein Y preferably comprises Si, and wherein even more preferably Y is Si.

According to the inventive process for the preparation of a zeolitic material having a CHA framework structure, one or more structure directing agents are optionally provided in step (1). In particular, depending on the one or more zeolitic materials which are comprised in the shell portion which in step (2) is crystallized on the seed crystals provided in step (1), it may be necessary or advantageous to provide one or more structure directing agents in the mixture of step (1) for respectively enabling or enhancing the crystallization the one or more of the zeolitic materials of the shell portion of the zeolite crystals in step (2) of the inventive process. Within the meaning of the present invention, the term "structure directing agent" refers to any compound or combination of compounds which enables and/or may enhance the formation of a zeolitic material according to the present invention having a CHA framework structure which is crystallized in step (2) on the seed crystals provided in step (1) and which, in particular, enables or enhances the formation of the characteristic microporous structure of the zeolitic material crystallized in step 2. Thus, in principle, any suitable structure directing agent may be provided in the mixture of step (1), provided that one or more zeolitic materials may be crystallized in step (2) of the inventive process on the seed crystal provided in the mixture of step (1) thus forming the shell of the zeolite crystals. Thus, by way of example, the one or more structure directing agents provided in step (1) may be any suitable organotemplate, wherein preferably the one or more structure directing agents comprise one or more compounds selected from the group consisting of tetraalkylammonium compounds, dialkyl amines, heterocyclic amines, and combinations of two or more thereof. More preferably, the one or more structure directing agents comprise one or more compounds selected from the group consisting of tetra($C_1$-$C_5$)alkylammonium compounds, di($C_1$-$C_5$)alkyl amines, oxygen containing heteroxyclic amines with 5 to 8 ring members, and combinations of two or more thereof, more preferably from the group consisting of tetra($C_2$-$C_4$)alkylammonium compounds, di($C_2$-$C_4$)alkyl amines, oxygen containing heteroxyclic amines with 5 to 7 ring members, and combinations of two or more thereof, more preferably from the group consisting of tetra($C_2$-$C_3$)alkylammonium compounds, di($C_2$-$C_3$) alkyl amines, oxygen containing heteroxyclic amines with 5 or 6 ring members, and combinations of two or more thereof. According to particularly preferred embodiments, the one or more structure directing agents optionally provided in step (1) comprises one or more compounds selected from the group consisting of tetraethylammonium salts, preferably tetraethylammonium hydroxide, diethyl amine, isopropylamine, di-n-propylamine, morpholine, and combinations of two or more thereof, wherein more preferably the one or more structure directing agents comprise diethyl amine and/or morpholine, and wherein even more preferably the structure directing agent is diethyl amine and/or morpholine.

Thus, according to certain embodiments of the present invention wherein the mixture provided in step (1) comprises one or more structure directing agents, it is preferred that the structure directing agent comprises one or more compounds selected from the group consisting of tetraalkylammonium compounds, dialkyl amines, heterocyclic amines, and combinations of two or more thereof, preferably from the group consisting of tetra($C_1$-$C_5$)alkylammonium compounds, di($C_1$-$C_5$)alkyl amines, oxygen containing heteroxyclic amines with 5 to 8 ring members, and combinations of two or more thereof, more preferably from the group consisting of tetra($C_2$-$C_4$)alkylammonium compounds, di($C_2$-$C_4$)alkyl amines, oxygen containing heteroxyclic amines with 5 to 7 ring members, and combinations of two or more thereof, more preferably from the group consisting of tetra($C_2$-$C_3$) alkylammonium compounds, di($C_2$-$C_3$)alkyl amines, oxygen containing heteroxyclic amines with 5 or 6 ring members, and combinations of two or more thereof, wherein more preferably the structure directing agent comprises one or more compounds selected from the group consisting of tetraethylammonium salts, preferably tetraethylammonium hydroxide, diethyl amine, isopropylamine, di-n-propylamine, morpholine, and combinations of two or more thereof, and wherein even more preferably the structure directing agent comprises diethyl amine and/or morpholine, the structure directing agent preferably being diethyl amine and/or morpholine.

According to certain embodiments of the inventive process, the mixture provided in step (1) comprises seed crystals having a CHA framework structure, wherein the CHA framework structure of the seed crystals comprises $YO_2$, and $X_2O_3$, and wherein the seed crystals have a diameter of 450 nm or greater. In particular, it has surprisingly been found that by using seed crystals having the aforementioned characteristics in the inventive process, a zeolitic material having a CHA framework structure may be obtained, wherein said zeolitic material comprises zeolite crystals having a core-shell structure. More specifically, by employing seed crystals of a certain size, said seeding material does not merely serve as a nucleating agent for the crystallization of a further zeolitic material as the desired product, but actually remains present in the zeolite crystals to form a core portion. Thus, instead of merely assisting the production of a further zeolitic material, the seed crystals of the inventive process are chosen such that they may form a constituent portion of the zeolite crystals obtained, as a result of which a novel zeolitic material may be obtained displaying unprecedented physical and chemical properties.

Thus, regarding the dimensions of the seed crystals having a CHA framework structure provided in step (1), there is no general restriction as to their size, provided that the seed crystals have a diameter of 450 nm or greater. According to the present invention, the diameter of the seed crystals generally refers to their largest dimension, wherein according to a preferred meaning of the present invention, the diameter of the seed crystals refers to the average diameter of a seed crystal, and in particular is equal to the sum of the largest and smallest dimension thereof divided by two, thus giving the average of largest and smallest dimensions. Alternatively, the diameter of the seed crystals refers to their weight based particle size being the diameter of the sphere which has the same weight as a given particle. According to a particularly preferred meaning of the present invention, however, the diameter of the seed crystals refers to the smallest dimension of the seed crystal. Within the meaning of the present invention, the dimensions of a crystal preferably refer to its dimensions as obtained from scanning electron microscopy (SEM).

Although there is no general limit as to the maximum size or diameter with respect to the diameter which the seed crystals display, it is preferred according to the inventive process that the seed crystals display a diameter comprised in the range of from 450 nm to 50 µm, wherein more preferably the diameter of the seed crystals is comprised in the range of from 500 nm to 45 µm, more preferably of from 700 nm to 30 µm, more preferably of from 900 nm to 20 µm, more preferably of from 1.1 to 15 µm, more preferably of from 1.5 to 10 µm, more preferably of from 1.8 to 7 µm, more preferably of from 2 to 5 µm, and even more preferably of from 2.3 to 4 µm. According to particularly preferred embodiments of the present invention, the seed crystals comprised in the mixture of step (1) have a diameter comprised in the range of from 2.5 to 3.5 µm.

Thus, according to one or more embodiments of the inventive process, the seed crystals provided in step (1) have a diameter comprised in the range of from 450 nm to 50 µm, preferably of from 500 nm to 45 µm, preferably of from 700 nm to 30 µm, more preferably of from 900 nm to 20 µm, more preferably of from 1.1 to 15 µm, more preferably of from 1.5 to 10 µm, more preferably of from 1.8 to 7 µm, more preferably of from 2 to 5 µm, more preferably of from 2.3 to 4 µm, and even more preferably of from 2.5 to 3.5 µm.

As concerns the amount of seed crystals which are provided in step (1) of the inventive process, any suitable amount may be used, provided that a zeolitic material comprising zeolite crystals having a core-shell structure may be obtained from crystallization in step (2). Thus, by way of example, the amount of seed crystals provided in the mixture may range anywhere from 1 to 90 wt.-% based on 100 wt.-% of the total amount of $X_2O_3$, $Z_2O_5$, and optional $YO_2$ respectively comprised in the one or more sources for $X_2O_3$, $Z_2O_5$, and optionally preferred $YO_2$ provided in the mixture of step (1), wherein preferably the amount of seed crystals is comprised in the range of from 3-70 wt.-%, more preferably of from 5-50 wt.-%, more preferably of from 6-30 wt.-%, more preferably of from 7-15 wt.-%, and even more preferably of from 8-12 wt.-%. According to particularly preferred embodiments of the present invention, the amount of seed crystals provided in step (1) based on 100% of the total amount of $X_2O_3$, $Z_2O_5$, and optional $YO_2$ respectively comprised in the one or more sources for $X_2O_3$, $Z_2O_5$, and optionally preferred $YO_2$, is from 9-11 wt.-%.

Therefore, according to one or more embodiments of the inventive process, the amount of seed crystals in the mixture provided in step (1) ranges from 1-90 wt.-% based on 100 wt.-% of the total amount of $X_2O_3$, $Z_2O_5$, and optional $YO_2$ respectively comprised in the one or more sources for $X_2O_3$, $Z_2O_5$, and optionally preferred $YO_2$, preferably from 3-70 wt.-%, more preferably from 5-50 wt.-%, more preferably from 6-30 wt.-%, more preferably from 7-15 wt.-%, more preferably from 8-12 wt.-%, and even more preferably from 9-11 wt.-%.

Regarding the composition of the seed crystals having a CHA framework structure, there is no particular restriction as to their composition, provided that they comprise $YO_2$ and $X_2O_3$, wherein Y is a tetravalent element and X is a trivalent element, and provided that they are suitable for forming the core portion of the zeolite crystals having a core-shell structure obtained from crystallization in step (2) of the inventive process. As defined in the foregoing with respect to the inventive process, $YO_2$ and $X_2O_3$ comprised in the framework structure of the seed crystals having a CHA framework structure is contained therein as structure building elements, as opposed to non-framework elements which can be present in the pores and/or cavities formed by the CHA framework structure and typical for zeolitic materials in general.

In principle, the seed crystals having a CHA framework structure may comprise any conceivable tetravalent element Y, wherein Y stands for one or several tetravalent elements. Preferred tetravalent elements comprised in the seed crystals according to the present invention include Si, Sn, Ti, Zr, and Ge, and combinations of two or more thereof. More preferably, Y stands for Si, Ti, or Zr, or any combination of said tetravalent elements, even more preferably for Si and/or Sn.

According to the present invention, it is particularly preferred that Y stands for Si.

According to certain embodiments of the inventive process wherein one or more sources for $YO_2$ are further provided in step (1), it is further preferred that both said one or more sources for $YO_2$ and the seed crystals having a CHA framework structure provided in step (1) comprise the same one or more tetravalent elements, wherein even more preferably Y comprised in the one or more sources for $YO_2$ and Y comprised in the seed crystals having a CHA framework structure stand for the same one or more tetravalent elements.

Thus, according to certain embodiments of the inventive process, embodiments are preferred wherein Y comprised in the seed crystals and/or (preferably and), wherein Y preferably further provided in step (1) in the one or more sources for $YO_2$ are, independently from one another, selected from the group consisting of Si, Sn, Ti, Zr, Ge, and combinations of two or more thereof, wherein Y preferably comprises Si, and wherein even more preferably Y is Si.

Furthermore, the seed crystals having a CHA framework structure may comprise any suitable trivalent element X, wherein again X stands for either one or several trivalent elements. Preferred trivalent elements according to the present invention include Al, B, In, and Ga, and combinations thereof. More preferably, X comprises Al or Ga, wherein more preferably X comprises Al, and wherein even more preferably X is Al.

According to one or more embodiments of the inventive process, it is further preferred that both said one or more sources for $X_2O_3$ and the seed crystals having a CHA framework structure provided in step (1) comprise the same one or more trivalent elements X, wherein even more preferably X comprised in the one or more sources for $X_2O_3$ and X comprised in the seed crystals having a CHA framework structure stand for the same one or more trivalent elements.

Therefore, according to the inventive process, embodiments are preferred wherein X comprised in the seed crystals and/or (preferably and) wherein X provided in step (1) in the one or more sources for $X_2O_3$ are, independently from one another, selected from the group consisting of Al, B, In, Ga, and combinations of two or more thereof, wherein X preferably comprises Al or Ga, wherein more preferably X comprises Al, and wherein even more preferably X is Al.

According to certain embodiments of the inventive process, the seed crystals having a CHA framework structure may optionally further comprise $Z_2O_5$, wherein Z stands for any conceivable pentavalent element, Z standing for either one or several pentavalent elements. As defined in the foregoing with respect to the inventive process, $Z_2O_5$ which is optionally comprised in the framework structure of the seed crystals having a CHA framework structure is contained therein as structure building element, as opposed to non-framework elements which can be present in the pores and/or cavities formed by the CHA framework structure and typical for zeolitic materials in general. Preferred pentavalent elements Z according to the present invention include P, As, Sb, Bi, V, Nb, Ta, and mixtures of two or more thereof. More preferably, Z stands for one or more elements selected from the group consisting of P, As, V, and mixtures of two or more thereof, wherein more preferably Z comprises P or As. According to particularly preferred embodiments thereof, Z comprises P, wherein it is particularly preferred that Z is P.

According to certain embodiments of the inventive process wherein the CHA framework structure of the seed crystals further comprises $Z_2O_5$, it is further preferred that both the seed crystals and the one or more sources for $Z_2O_5$ provided in step (1) comprise the same one or more pentavalent elements, wherein even more preferably Z comprised in the one or more sources for $Z_2O_5$ and Z comprised in the seed crystals having a CHA framework structure stand for the same one or more pentavalent elements.

Thus, according to the inventive process, embodiments are included wherein Z optionally comprised in the seed crystals and/or (preferably and) wherein Z provided in step (1) in the one or more sources for $Z_2O_5$ are, independently from one another, selected from the group consisting of P, As, Sb, Bi, V, Nb, Ta, and combinations of two or more thereof, preferably from the group consisting of P, As, V, and combinations of two or more thereof, wherein more preferably Z comprises P or As, preferably P, and wherein even more preferably Z is P.

As regards the Y:X molar ratio of the seed crystals provided in step (1) of the inventive process, there is again no particular restriction in this respect, provided that Y:X molar ratio of the seed crystals are suitable for forming the core portion of the zeolite crystals having a core-shell structure obtained from crystallization in step (2) of the inventive process. Thus, by way of example, the seed crystals provided in step (1) of the inventive process may display a Y:X molar ratio comprised in the range of anywhere from 1 to 100, wherein it is preferred that the molar ratio displayed by the seed crystals is comprised in the range of from 5 to 50, more preferably of from 10 to 30, more preferably of from 15 to 20, and even more preferably of from 16 to 18. According to particularly preferred embodiments of the present invention, the Y:X molar ratio of the seed crystals is comprised in the range of from 16.5 to 17.

In instances wherein the seed crystals further comprise $Z_2O_5$ in addition to $YO_2$ and $X_2O_3$, the given seed crystals accordingly display a ratio of one or more tetravalent elements Y to one or more trivalent elements X to one or more pentavalent elements Z which may be expressed in terms of a Y:nX:pZ molar ratio, wherein n and p respectively stand for a positive natural number. As for the Y:X molar ratio of seed crystals not further comprising $Z_2O_5$, there is no particular restriction as to the Y:nX:pZ molar ratio of seed crystals having the CHA framework structure further comprising $Z_2O_5$ which may be used in the inventive process, provided that said seed crystals are suitable for forming the core portion of the zeolite crystals having a core-shell structure obtained from crystallization in step (2) of the inventive process. According to embodiments of the present invention wherein the seed crystals provided in step (1) further comprise $Z_2O_5$ in the CHA framework structure it is however preferred that the value for the ratio $(1+2p):(n-p)$ is comprised in the range of from 1 to 100, and more preferably in the range of from 5 to 50, more preferably of from 10 to 30, more preferably of from 15 to 20, and even more preferably of from 16 to 18. According to particularly preferred embodiments of the present invention, the ratio $(1+2p):(n-p)$ of the Y:nX:pZ molar ratio of seed crystals having the CHA framework structure further comprising $Z_2O_5$ is comprised in the range of from 16.5 to 17.

Therefore, according to the inventive process, embodiments are further preferred wherein the CHA framework structure of the seed crystals provided in step (1) displays a Y:X molar ratio comprised in the range of from 1 to 100, preferably of from 5 to 50, more preferably of from 10 to 30, more preferably of from 15 to 20, more preferably of from 16 to 18, and even more preferably of from 16.5 to 17, and wherein if the CHA framework structure of the seed crystals further comprises $Z_2O_5$ in addition to $YO_2$ and $X_2O_3$, the seed crystals display a Y:nX:pZ molar ratio, wherein the value for the ratio (1+2p):(n−p) is comprised in the range of from 1 to 100, preferably of from 5 to 50, more preferably of from 10 to 30, more preferably of from 15 to 20, more preferably of from 16 to 18, and even more preferably of from 16.5 to 17.

According to particular embodiments of the present invention, the CHA framework structure of the seed crystals provided in step (1) of the inventive process does not comprise $Z_2O_5$ in addition to $X_2O_3$ and $YO_2$.

As concerns the specific type of seed crystals which may be used in the inventive process, there is again no particular limitation in this respect provided that the specific type of seed crystals having the CHA framework structure which are chosen are suitable for forming the core portion of the zeolite crystals having a core-shell structure obtained from crystallization in step (2) of the inventive process. Thus, by mere way of example, the seed crystals having a CHA framework structure may comprise one or more zeolites selected from the group consisting of (Ni(deta)$_2$)-UT-6, Chabazite, |Li—Na| [Al—Si—O]-CHA, DAF-5, Dehyd. Na-Chabazite, K-Chabazite (Iran), LZ-218, Linde D, Linde R, MeAPSO-47, Phi, SAPO-34, SAPO-47, SSZ-13, SSZ-62, UiO-21, Willhendersonite, ZK-14, ZYT-6, and combinations of two or more thereof. According to the present invention it is however preferred that the seed crystals comprise one or more zeolites selected from the group consisting of Ni(deta)$_2$)-UT-6, Chabazite, |Li—Na| [Al—Si—O]-CHA, DAF-5, Dehyd. Na-Chabazite, K-Chabazite (Iran), LZ-218, Linde D, Linde R, Phi, SSZ-13, SSZ-62, UiO-21, Willhendersonite, ZK-14, ZYT-6, and combinations of two or more thereof. According to particularly preferred embodiments of the present invention, the seed crystals comprise SSZ-13, wherein even more preferably SSZ-13 is employed as seed crystals in the inventive process.

Thus, according to one or more embodiments of the present invention, the seed crystals provided in step (1) of the inventive process comprise one or more zeolites selected from the group consisting of (Ni(deta)$_2$)-UT-6, Chabazite, |Li—Na| [Al—Si—O]-CHA, DAF-5, Dehyd. Na-Chabazite, K-Chabazite (Iran), LZ-218, Linde D, Linde R, MeAPSO-47, Phi, SAPO-34, SAPO-47, SSZ-13, SSZ-62, UiO-21, Willhendersonite, ZK-14, ZYT-6, and combinations of two or more thereof,
preferably from the group consisting of (Ni(deta)$_2$)-UT-6, Chabazite, |Li—Na| [Al—Si—O]-CHA, DAF-5, Dehyd. Na-Chabazite, K-Chabazite (Iran), LZ-218, Linde D, Linde R, Phi, SSZ-13, SSZ-62, UiO-21, Willhendersonite, ZK-14, ZYT-6, and combinations of two or more thereof, and
wherein even more preferably the seed crystals comprise SSZ-13.

According to certain embodiments of the process of the present invention one or more sources for $Z_2O_5$ can be provided in step (1) in any conceivable form, provided that a zeolitic material comprising zeolite crystals having a core-shell structure can be crystallized in step (2). Preferably, $Z_2O_5$ is provided as such and/or as a compound which comprises $Z_2O_5$ entirely or in part as a chemical moiety and/or as a compound which (partly or entirely) is chemically transformed such that it may be integrated as $Z_2O_5$ in the CHA framework structure crystallized in step (2) of the inventive process.

In embodiments of the present invention, wherein Z stands for P or for a combination of P with one or more further pentavalent elements, the source for $P_2O_5$ provided in step (1) can be any conceivable source. There can be used for example any type of phosphorous oxides, phosphates, acids of phosphorous, or mixtures thereof. Preferably the source for $Z_2O_5$ comprises at least one compound selected from the group consisting of phosphates, acids of phosphorous, and mixtures thereof, wherein even more preferably the one or more sources for $Z_2O_5$ provided in step (1) comprises one or more acids of phosphorous, preferably phosphoric acid. According to particularly preferred embodiments of the present invention, the source for $Z_2O_5$ is phosphoric acid.

Therefore, according to certain embodiments of the present invention, the one or more sources for $Z_2O_5$ comprises one or more phosphates and/or one or more oxides and/or one or more acids of phosphorous, preferably one or more acids of phosphorous, more preferably phosphoric acid, and wherein even more preferably the source for $Z_2O_5$ is phosphoric acid.

According to the inventive process, there is also no particular restriction as to the one or more sources for $X_2O_3$ which are provided in step (1), provided that a zeolitic material having a core-shell structure may be obtained from crystallization in step (2). Thus, $X_2O_3$ can be provided in as such and/or as a compound which comprises $X_2O_3$ as a chemical moiety and/or as a compound which (partly or entirely) is chemically transformed to $X_2O_3$ during the inventive process.

In embodiments of the present invention, wherein X stands for Al or for a combination of Al with one or more further trivalent elements, the source for $Al_2O_3$ provided in step (1) can be any conceivable source. There can be used for example any type of alumina and aluminates, aluminum salts such as, for example, alkali metal aluminates, aluminum alcoholates, such as, for example, aluminum triisopropylate, or hydrated alumina such as, for example, alumina trihydrate, or mixtures thereof. Preferably, the source for $Al_2O_3$ comprises at least one compound selected from the group consisting aluminate salts, aluminum hydroxides, aluminum oxide hydroxides, and mixtures of two or more thereof, and more preferably from the group consisting of aluminum hydroxides, aluminum oxide hydroxides, and mixtures of two or more thereof, wherein more preferably the one or more sources for $Al_2O_3$ comprises one or more aluminum oxide hydroxides, preferably boehmite and/or diaspora. According to particularly preferred embodiments of the present invention, the one or more sources for and more preferably boehmite, and wherein even more preferably the source for $Al_2O_3$ is boehmite According to embodiments of the present invention wherein X stands for B or for a combination of B with one or more further trivalent elements, the source for $B_2O_3$ provided in step (1) can again be any conceivable source. By way of example, free boric acid and/or borates and/or boric esters may be provided as the source for $B_2O_3$, such as, for example, triethyl borate or trimethyl borate. According to the present invention it is preferred that the source for $B_2O_3$ comprises one or more boron containing compounds selected from the group consisting of free boric acid, borates, boric esters, and mixtures of two or more thereof, preferably from the group consisting of boric acid, borates, and mixtures of two or more thereof. In particularly preferred embodiments of the present invention, the source for $B_2O_3$ is boric acid.

Therefore, according to particular embodiments of the inventive process, the one or more sources for $X_2O_3$ comprises one or more compounds selected from the group consisting of aluminate salts, aluminum hydroxides, aluminum oxide hydroxides, and mixtures of two or more thereof, preferably from the group consisting of aluminum hydroxides, aluminum oxide hydroxides, and mixtures of two or more thereof, wherein more preferably the one or more sources for $X_2O_3$ comprises one or more aluminum oxide hydroxides, preferably boehmite and/or diaspore, and more preferably boehmite, and wherein even more preferably the source for $X_2O_3$ is boehmite.

Furthermore, according to embodiments of the inventive process wherein one or more sources for $YO_2$ are provided in step (1), $YO_2$ may be provided in any conceivable form, provided that a zeolitic material comprising zeolite crystals having a core-shell structure can be obtained from crystallization in step (2). Preferably, $YO_2$ is provided as such and/or as a compound which comprises $YO_2$ as a chemical moiety and/or as a compound which (partly or entirely) is chemically transformed to $YO_2$ during the inventive process.

In embodiments of the present invention, wherein Y stands for Si or for a combination of Si with one or more further tetravalent elements, the source for $SiO_2$ preferably provided in step (1) can be any conceivable source. There can therefore be used, for example, all types of silica and/or silicates, preferably fumed silica, silica hydrosols, reactive amorphous solid silicas, silica gel, silicic acid, water glass, sodium metasilicate hydrate, sesquisilicate or disilicate, colloidal silica, pyrogenic silica, silicic acid esters, or tetraalkoxysilanes, or mixtures of at least two of these compounds. Among the silicates which may be employed, alkali metal silicates are preferred, more preferably water glass, more preferably sodium and/or potassium silicate, and even more preferably sodium silicate. Among the silica which may be employed, fumed silica is preferred. According to particularly preferred embodiments the at least one source for $SiO_2$ comprises silica, preferably fumed silica. According to the present invention, the one or more sources for $SiO_2$ preferably provided as $YO_2$ in the mixture of step (1) preferably comprise one or more silicas as the one or more sources for $SiO_2$, wherein more preferably the one or more sources for $SiO_2$ comprise fumed silica. According to particularly preferred embodiments of the present invention, fumed silica is provided in step (1) as the one or more sources for $YO_2$.

Therefore, according to particular embodiments of the inventive process, the one or more sources for $YO_2$ provided in step (1) comprises one or more compounds selected from the group consisting of silicas, silicates, and mixtures of two or more thereof, wherein preferably the one or more sources for $YO_2$ comprise one or more silicas, wherein more preferably the one or more sources for $YO_2$ comprise fumed silica, and wherein even more preferably the source for $YO_2$ is fumed silica.

In general, according to the present invention, the $X_2O_3:Z_2O_5$ molar ratio of the mixture provided in step (1) can have any conceivable value, provided that a zeolitic material comprising zeolite crystals having a core-shell structure can be obtained from crystallization in step (2). Generally, the molar ratio ranges anywhere from 1:(0.05-30). According to the present invention it is however preferred that the $X_2O_3:Z_2O_5$ molar ratio of the mixture provided in step (1) is comprised in the range of from 1:(0.1-15), more preferably of from 1:(0.2-10), more preferably of from 1:(0.5-5), and even more preferably of from 1:(0.8-3). It is particularly preferred according to the inventive process that the $X_2O_3:Z_2O_5$ molar ratio of the mixture provided in step (1) is comprised in the range of from 1:(1-2.5).

According to embodiments of the inventive process wherein the mixture in step (1) further comprises one or more sources for $YO_2$, as for the $X_2O_3:Z_2O_5$ molar ratio, the $YO_2:X_2O_3:Z_2O_5$ molar ratio according to said preferred embodiments with respect to the mixture provided in step (1) can have any conceivable value, provided that a zeolitic material comprising zeolite crystals having a core-shell structure can be obtained from crystallization in step (2). Thus, by way of example, the $YO_2:X_2O_3:Z_2O_5$ molar ratio according to said preferred embodiments may be comprised in the range of anywhere from (0.01-10):1:(0.05-30), wherein preferably, the $YO_2:X_2O_3:Z_2O_5$ molar ratio is comprised in the range of from (0.05-5):1:(0.1-15), more preferably of from (0.1-2):1:(0.2-10), more preferably of from (0.3-1):1:(0.5-5), and even more preferably for from (0.5-0.7):1:(0.8-3). According to particularly preferred embodiments thereof, the $YO_2:X_2O_3:Z_2O_5$ molar ratio is comprised in the range of from (0.55-0.65):1:(1-2.5).

Thus, according to the present invention, embodiments of the inventive process are preferred wherein the $X_2O_3:Z_2O_5$ molar ratio of the mixture provided in step (1) is comprised in the range of 1:(0.05-30), preferably 1:(0.1-15), more preferably 1:(0.2-10), more preferably 1:(0.5-5), more preferably 1:(0.8-3), and even more preferably 1:(1-2.5), and
wherein if the mixture provided in step (1) further comprises $YO_2$, the $YO_2:X_2O_3:Z_2O_5$ molar ratio of the mixture provided in step (1) is comprised in the range of (0.01-10):1:(0.05-30), preferably (0.05-5):1:(0.1-15), more preferably (0.1-2):1:(0.2-10), more preferably (0.3-1):1:(0.5-5), more preferably (0.5-0.7):1:(0.8-3), and even more preferably (0.55-0.65):1:(1-2.5).

As regards the zeolitic material which is crystallized in step (2) of the inventive process onto the seed crystals thus forming the shell portion of the zeolite crystals having a core-shell structure, there is no particular restriction according to the present invention as to the particular type of zeolitic material which may be crystallized as the shell portion, provided that is has a CHA framework structure. Thus, by way of example, the zeolitic material crystallized onto the seed crystals in step (2) of the inventive process may comprise one or more zeolites selected from the group consisting of [Al—As—O]-CHA, [Al—Co—P—O]-CHA, [Co—Al—P—O]-CHA, [Mg—Al—P—O]-CHA, [Zn—Al—P—O]-CHA, AlPO-34, CoAPO-44, CoAPO-47, GaPO-34, MeAPO-47, MeAPSO-47, SAPO-34, SAPO-47, ZYT-6, and combinations of two or more thereof. According to the present invention it is however preferred that the zeolitic material crystallized onto the seed crystals in step (2) of the inventive process comprise one or more zeolites selected from the group consisting of MeAPSO-47, SAPO-34, SAPO-47, ZYT-6, and combinations of two or more thereof, wherein even more preferably the zeolitic material crystallized as the shell-portion in step (2) of the inventive process comprises SAPO-34. According to a particularly preferred embodiment of the present invention, SAPO-34 is crystallized in step (2) of the inventive process onto the seed crystals provided in step (1).

Thus, according to particular embodiments of the inventive process, the zeolitic material having a CHA framework structure crystallized in step (2) comprises one or more zeolites selected from the group consisting of [Al—As—O]-CHA, [Al—Co—P—O]-CHA, [Co—Al—P—O]-CHA, [Mg—Al—P—O]-CHA, [Zn—Al—P—O]-CHA, AlPO-34, CoAPO-44, CoAPO-47, GaPO-34, MeAPO-47, MeAPSO-47, SAPO-34, SAPO-47, ZYT-6, and combinations of two or more thereof, preferably from the group consisting of MeAPSO-47, SAPO-34, SAPO-47, ZYT-6, and combinations of two or more thereof, wherein even more preferably the shell-portion of the zeolite crystals comprise SAPO-34.

In step (1) according to the present invention, the mixture can be prepared by any conceivable means, wherein mixing by agitation is preferred, preferably by means of stirring.

According to the present invention, the mixture according to step (1) of the inventive process preferably further comprises one or more solvents. In this respect, any conceivable solvents may be used in any conceivable amount, provided that a zeolitic material comprising zeolite crystals having a core-shell structure can be obtained from crystallization in step (2). Thus, by way of example, the one or more solvents may be chosen from water, organic solvents, and mixtures thereof, preferably from the group consisting of distilled water, alcohols, and mixtures thereof, more preferably from the group consisting of distilled water, methanol, ethanol, propanol, and mixtures thereof. According to particularly preferred embodiments of the present invention, only water and preferably only distilled water is contained in the mixture according to step (1) as the solvent.

Therefore, according to one or more embodiments of the inventive process, the mixture provided in step (1) further comprises a solvent, wherein said solvent preferably comprises water, more preferably distilled water, wherein even more preferably the solvent is water, preferably distilled water.

As regards the one or more solvents which may be provided in the mixture according to step (1), any suitable amount thereof may be used in the mixture, provided that a zeolitic material comprising zeolite crystals having a core-shell structure can be obtained from crystallization in step (2). Thus, by way of example, the $H_2O:Z_2O_5$ molar ratio of the mixture provided in step (1), wherein $Z_2O_5$ stands for the molar amount of $Z_2O_5$ contained in the at least one source for $Z_2O_5$ provided in step (1), may range anywhere from 5 to 100. According to the present invention it is however preferred that the $H_2O:Z_2O_5$ molar ratio of the mixture ranges from 10 to 70, more preferably from 15 to 50, and even more preferably from 20 to 45. According to particularly preferred embodiments, the $H_2O:Z_2O_5$ molar ratio of the mixture provided in step (1) ranges from 23 to 41.

Same applies according with respect to the $H_2O:X_2O_3$ molar ratio of the mixture provided in step (1), which may have any suitable value provided that a zeolitic material comprising zeolite crystals having a core-shell structure can be obtained from crystallization in step (2). Thus, by way of example, the $H_2O:X_2O_3$ molar ratio of the mixture provided in step (1), wherein $X_2O_3$ stands for the molar amount of $X_2O_3$ contained in the at least one source for $X_2O_3$ provided in step (1), may range anywhere from 5 to 150. According to the present invention it is however preferred that the $H_2O:X_2O_3$ molar ratio of the mixture ranges from 10 to 100, more preferably from 30 to 70, and even more preferably from 35-60. According to particularly preferred embodiments, the $H_2O:Z_2O_5$ molar ratio of the mixture provided in step (1) ranges from 40 to 53.

Thus, according to particular embodiments of the inventive process, the $H_2O:Z_2O_5$ molar ratio of the mixture according to step (1) ranges from 5-100, preferably from 10-70, more preferably from 15-50, more preferably from 20-45, and even more preferably from 23-41,
and/or (preferably and),
wherein the $H_2O:X_2O_3$ molar ratio of the mixture according to step (1) ranges from 5-150, preferably from 10-100, more preferably from 30-70, more preferably from 35-60, and even more preferably from 40-53.

In general, the single components for providing the mixture of step (1) of the inventive process can be added in any order, provided that a zeolitic material comprising zeolite crystals having a core-shell structure can be obtained from crystallization in step (2). This may, by way of example, involve the addition of the optional solvent and the one or more sources for $X_2O_3$, followed by the addition of the one or more sources for $Z_2O_5$, after which according to preferred embodiments the one or more sources for $YO_2$ is then added, after which the optional one or more structure directing agents are added, and after which finally the seed crystals having a CHA framework structure are added for obtaining a mixture according to step (1) of the inventive process.

In general, step (2) according to the inventive process can be conducted in any conceivable manner, provided that a zeolitic material comprising zeolite crystals having a core-shell structure can be obtained from crystallization of the mixture provided in step (1). Thus, the mixture can be crystallized in any suitable type of vessel, wherein a means of agitation is optionally employed, preferably by rotation of the vessel and/or stirring, and more preferably by stirring the mixture. According to the inventive process, crystallization in step (2) may also be conducted under static conditions.

According to the inventive process, the mixture is may be heated during at least a portion of the crystallization process in step (2). In general, the mixture can be heated to any conceivable temperature of crystallization, provided that a zeolitic material comprising zeolite crystals having a core-shell structure can be crystallized from the mixture. Thus, by way of example the mixture in step (2) may be heated to a temperature ranging anywhere from 80 to 270° C. According to the invention it is however preferred that the temperature be comprised in the range of from 100 to 250° C., more preferably from 130 to 240° C., more preferably from 150 to 230° C., more preferably from 180 to 220° C., and even more preferably from 190 to 210° C. According to particularly preferred embodiments, the crystallization process in step (2) involves heating the mixture to a temperature comprised in the range of from 195 to 205° C. According to further embodiments of the present invention which are alternatively preferred, the crystallization in step (2) involves heating of the mixture, 180° C. to 270° C., more preferably from 180 to 250° C., more preferably from 180 to 240° C., more preferably from 185 to 230° C., more preferably from 185 to 220° C., more preferably from 190 to 210° C., and even more preferably from 195 to 205° C.

Thus, according to certain embodiments of the inventive process it is preferred that the crystallization in step (2) involves heating of the mixture, preferably at a temperature ranging from 80 to 270° C., more preferably from 100 to 250° C., more preferably from 130 to 240° C., more preferably from 150 to 230° C., more preferably from 180 to 220° C., more preferably from 190 to 210° C., and even more preferably from 195 to 205° C.

The heating in step (2) of the inventive process can be conducted in any conceivable manner provided that a zeolitic material comprising zeolite crystals having a core-shell structure can be obtained from crystallization of the mixture provided in step (1). In general, heating may be conducted at one temperature of crystallization or vary between different temperatures. Preferably, a heat ramp is used for reaching the temperature of crystallization, wherein the heating rate preferably ranges from 10 to 100° C./h, more preferably from 20 to 70° C./h, more preferably from 25 to 60° C./h, more preferably from 30 to 50° C./h, and even more preferably from 35 to 45° C./h.

In particular embodiments of the present invention, the mixture according to step (1) is subjected in step (2) to a pressure which is elevated with regard to normal pressure. The term "normal pressure" as used in the context of the present invention relates to a pressure of 101,325 Pa in the ideal case. However, this pressure may vary within boundaries known to the person skilled in the art. By way of example, this pressure can be in the range of from 95,000 to 106,000 or of from 96,000 to 105,000 or of from 97,000 to 104,000 or of from 98,000 to 103,000 or of from 99,000 to 102,000 Pa.

In embodiments of the inventive process wherein a solvent is present in the mixture according to step (1), it is furthermore preferred that heating in step (2) is conducted under solvothermal conditions, meaning that the mixture is crystallized under autogenous pressure of the solvent which is used, for example by conducting heating in an autoclave or other crystallization vessel suited for generating solvothermal conditions. In particularly preferred embodiments wherein the solvent comprises water, preferably distilled water, heating in step (2) is accordingly preferably conducted under hydrothermal conditions.

Therefore, according to one or more embodiments of the inventive process, the heating in step (2) is conducted under autogenous pressure, preferably under solvothermal conditions, and more preferably under hydrothermal conditions.

The apparatus which can be used in the present invention for crystallization is not particularly restricted, provided that the desired parameters for the crystallization process can be realized, in particular with respect to the preferred embodiments requiring particular crystallization conditions. In the preferred embodiments conducted under solvothermal conditions, any type of autoclave or digestion vessel can be used, wherein a Teflon-lined apparatus is preferred.

In general, the duration of the crystallization process in step (2) of the inventive process is not particularly limited, provided that a zeolitic material comprising zeolite crystals having a core-shell structure can be obtained from crystallization of the mixture provided in step (1).

Thus, by way of example, the duration of the crystallization process in step (2) may be comprised in the range of from 1 to 50 h. According to the inventive process it is however preferred that the duration of the crystallization process in step (2) ranges from 1.5 to 30 h, more preferably from 1.5 to 20 h, more preferably from 2 to 13 h, more preferably from 2 to 9 h, more preferably from 2 to 6 h, and even more preferably from 2 to 4 h. According to particularly preferred embodiments of the inventive process, the duration of the crystallization process in step (2) ranges from 2.5 to 3.5 h. According to further embodiments of the present invention which are alternatively preferred, the duration of the crystallization process in step (2) ranges from 2 to 30 h, more preferably from 4 to 25 h, more preferably from 6 to 20 h, more preferably from 8 to 17 h, more preferably from 10 to 15 h, and even more preferably from 11 to 13 h.

Thus, as mentioned in the foregoing, it has surprisingly been found that by providing seed crystals having a CHA framework structure which have a certain size, it is actually possible to considerably shorten the crystallization period. Furthermore, by using short crystallization periods according to preferred and particularly preferred embodiments of the present invention, it may be assured that the seed crystals used in the inventive process are not significantly dissolved during crystallization, such that zeolite crystals having a core-shell structure may be obtained, and in particular such zeolite crystals having a core-shell structure according to particular and preferred embodiments of the present invention. More specifically, by using a short duration for the crystallization, zeolite crystals having a core portion according to particular and preferred embodiments of the present invention, in particular with respect to the size of the core portion, may be achieved, such as to assure the unique properties thereof due to the synergetic combination of the zeolitic materials comprised in the core and in the shell portions of the inventive material having a core-shell structure.

Thus, according to particular embodiments of the inventive process the crystallization in step (2) involves the heating of the mixture for a period ranging from 1 to 50 h, preferably from 1.5 to 30 h, more preferably from 1.5 to 20 h, more preferably from 2 to 13 h, more preferably from 2 to 9 h, more preferably from 2 to 6 h, more preferably from 2 to 4 h, and even more preferably from 2.5 to 3.5 h.

According to embodiments of the present invention, wherein the mixture is heated in step (2), said heating may be conducted during the entire crystallization process or during only one or more portions thereof, provided that a zeolitic material comprising zeolite crystals having a core-shell structure can be crystallized from the mixture provided in step (1). Preferably, heating is conducted during the entire duration of crystallization.

In general, the process of the present invention can optionally comprise further steps for the work-up and/or further physical and/or chemical transformation of the zeolitic material comprising zeolite crystals having a core-shell structure as obtained from crystallization in step (2). The crystallized material can for example be subject to any sequence of isolation and/or washing procedures and/or drying procedures and/or calcination procedures and/or ion-exchange procedures, wherein the zeolitic material obtained from crystallization in step (2) is preferably subject to at least one isolation and at least one washing procedure. Within the meaning of the present invention, the term "isolation" refers to a separation of the zeolitic material, and therefore refers to a "separation" or to a step of "separating" as defined in the present invention.

Therefore, according to one or more embodiments of the present invention the inventive process further comprises one or more of steps of (3) isolating the zeolitic material, preferably by filtration, and/or (4) washing the zeolitic material, and/or (5) drying the zeolitic material.

In step (3) of embodiments of the inventive process, the zeolitic material may be isolated from the reaction mixture obtained in step (2) by any conceivable means, wherein by way of example any means of filtration, ultrafiltration, diafiltration, centrifugation and/or decantation methods may be employed including combinations of two or more thereof. Furthermore, the filtration methods can involve suction and/or pressure filtration steps. According to particularly preferred embodiments of the present invention, the isolation of the zeolitic material in step (3) comprises one or more filtration steps, wherein more preferably the separation in step (3) is achieved by filtration.

With respect to one or more optional washing procedures in step (4), any conceivable solvent can be used. Washing agents which may be used are, for example, water, alcohols, such as methanol, ethanol or propanol, or mixtures of two or more thereof. Examples of mixtures are mixtures of two or more alcohols, such as methanol and ethanol or methanol and propanol or ethanol and propanol or methanol and ethanol and propanol, or mixtures of water and at least one alcohol, such as water and methanol or water and ethanol or water and propanol or water and methanol and ethanol or water and methanol and propanol or water and ethanol and propanol or water and methanol and ethanol and propanol. Water or a mixture of water and at least one alcohol, preferably water and ethanol, is preferred, distilled water being very particularly preferred as the only washing agent.

Preferably, the separated zeolitic material is washed until the pH of the washing agent, preferably the washwater, is in the range of from 6 to 8, preferably from 6.5 to 7.5, as determined via a standard glass electrode.

Furthermore, the inventive process can optionally comprise one or more drying steps. In general, any conceivable means of drying can be used. Drying procedures preferably include heating and/or applying vacuum to the zeolitic material comprising zeolite crystals having a core-shell structure.

In envisaged embodiments of the present invention, one or more drying steps may involve spray drying, preferably spray granulation of the zeolitic material.

In embodiments which comprise at least one drying step, the drying temperatures are preferably in the range of from 25° C. to 150° C., more preferably of from 60 to 140° C., more preferably of from 70 to 130° C. and even more preferably in the range of from 75 to 125° C. The durations of drying are preferably in the range of from 2 to 60 h, more preferably in the range of 6 to 48 hours, and even more preferably of from 12 to 24 h.

In general, the optional isolation and/or washing and/or drying procedures comprised in the inventive process can be conducted in any conceivably order and repeated one or more times.

Preferably, the inventive process comprises at least one step (3) of isolating at least a portion of the zeolitic material crystallized according to step (2), preferably by filtration thereof. According to the inventive process it is further preferred that after the at least one step of isolating, the zeolitic material is subject to at least one step of drying, wherein more preferably the zeolitic material is subject to at least one step of washing prior to the at least one drying step. In a particularly preferred embodiment, the zeolitic material crystallized according to step (2) is subject to at least one step (3) of isolating the zeolitic material from the reaction mixture obtained in step (2), followed by at least one step of washing, and then followed by at least one step of drying.

According to a further embodiment of the inventive process, the zeolitic material crystallized in step (2) is directly subject to at least one step of drying, preferably to spray drying and/or spray granulation, without isolating, washing, or drying of the zeolitic material beforehand. Directly subjecting the reaction mixture obtained from step (2) of the inventive process to a spray drying or spray granulation stage has the advantage that isolation and drying is performed in a single stage. Consequently, according to this embodiment of the present invention, an even more preferred process is provided wherein the number of post-synthesis workup steps is minimized, as a result of which material comprising zeolite crystals having a core-shell structure can be obtained from a highly simplified process.

In addition to or alternatively to one or more of the isolation, washing and/or drying procedures defined in optional steps (3), (4), and (5), the zeolitic material comprising zeolite crystals having a core-shell structure obtained in step (2) is preferably subject to a step (6) of calcination. In principle, calcination may be conducted at any conceivable temperature, provided that a thermally stable zeolitic material is obtained without substantial deterioration of the crystalline structure present in the zeolitic material as obtained in step (2). According to preferred embodiments, calcination of the zeolitic material is effected at a temperature comprised in the range of from 250 to 850° C., more preferably at a temperature of from 350 to 750° C., more preferably of from 450 to 650° C., more preferably of from 460 to 600° C., more preferably of from 470 to 560° C., and even more preferably of from 500 to 550° C.

According to embodiments of the present invention which include a step of calcining the zeolitic material obtained according to (2), there is no particular restriction as to when the step of calcining is conducted. Thus, by way of example, the zeolitic material obtained from step (2) of the inventive process may be subject to a calcination step (6) after having isolated the zeolitic material in one or more steps (3), preferably by one or more filtration steps. It is however preferred that after having been isolated, the zeolitic material is first subject to one or more washing step (4), preferably with distilled water, prior to being subject to a calcination procedure (6), wherein even more preferably the isolated and washed zeolitic material is further subject to one or more drying procedures (5) prior to subjecting said zeolitic material to a calcination procedure (6). Alternatively, the zeolitic material crystallized in step (2) may directly be subject to one or more drying steps (4), without isolating, washing, or drying the zeolitic material beforehand, after which it is then directly subject to a calcination procedure (6). According to said alternatively preferred embodiments, direct drying of the zeolitic material obtained from step (2) is preferably achieved by spray drying and/or spray granulation, even more preferably by spray granulation.

Therefore, according to particular embodiments, the inventive process further comprises one or more steps of
(6) calcining the zeolitic material obtained according to (2) or (3) or (4) or (5),
wherein the steps (3) and/or (4) and/or (5) and/or (6) can be conducted in any order, and wherein at least one of said steps is preferably repeated one or more times.

The present invention furthermore relates to a synthetic zeolitic material having a CHA framework structure, said zeolitic material comprising zeolite crystals having a core-shell structure, which is either obtained by the process according to the present invention or by any conceivable process which leads to a zeolitic material having a CHA framework structure, said zeolitic material comprising zeolite crystals having a core-shell structure, as obtainable according to the inventive process.

Therefore, the present invention also relates to a synthetic zeolitic material having a having a CHA framework structure, said zeolitic material comprising zeolite crystals having a core-shell structure, said material being obtainable and/or obtained, preferably obtained, according to the inventive process, and in particular according to preferred and particularly preferred embodiments thereof as defined in the present application.

Furthermore, the present invention relates to a zeolitic material having a CHA framework structure, said zeolitic material comprising zeolite crystals having a core-shell structure,
wherein
the core-portion of the zeolite crystals comprises $YO_2$, $X_2O_3$, and optionally $Z_2O_5$ in the zeolite framework structure of said core-portion, and wherein
the shell-portion of the zeolite crystals comprises $Z_2O_5$ and $X_2O_3$ in the zeolite framework structure of said shell-portion,
wherein Y is a tetravalent element, X is a trivalent element, and Z is a pentavalent element,
wherein the shell-portion preferably further comprises $YO_2$ in the zeolite framework structure of said shell-portion, and
wherein the core-portion displays a diameter of 450 nm or greater.

Thus, according to certain embodiments of the present invention, the zeolitic material having a CHA framework structure comprises zeolite crystals having a core-shell structure, wherein the core-portion comprises $YO_2$ and $X_2O_3$ in the CHA framework structure thereof. In particular, $YO_2$ and $X_2O_3$ comprised in the core-portion is contained in the framework structure of the zeolitic material having a CHA framework structure as structure building elements, as opposed to non-framework elements which can be present in the pores and/or cavities formed by the framework structure and typical for zeolitic materials in general.

In principle, the core-portion of the zeolite crystals having a CHA framework structure comprised in the zeolitic material of the present invention may comprise any conceivable tetravalent element Y, wherein Y stands for either one or several tetravalent elements. Preferred tetravalent elements according to the present invention include Si, Sn, Ti, Zr, and Ge, and combinations of two or more thereof. More preferably, Y stands for Si, Ti, or Zr, or any combination of said tetravalent elements, even more preferably for Si and/or Sn. According to the present invention, it is particularly preferred that Y stands for Si.

Furthermore, the core-portion of the zeolite crystals having a CHA framework structure comprised in the zeolitic material of the present invention may comprise any suitable trivalent element X, wherein again X stands for either one or several trivalent elements. Preferred trivalent elements according to the present invention include Al, B, In, and Ga, and combinations thereof. More preferably, X stands for Al or Ga. According to particularly preferred embodiments, X comprises Al, wherein it is particularly preferred that X stands for Al.

According to particular embodiments of the present invention, the core-portion of the zeolite crystals having a CHA framework structure comprised in the zeolitic material of the present invention further comprises $Z_2O_5$, wherein Z stands for any conceivably pentavalent element, Z standing for either one or several pentavalent elements. As defined in the foregoing with respect to $YO_2$ and $X_2O_3$, $Z_2O_5$ which is optionally comprised in the framework structure of the zeolitic material having a CHA framework structure is contained therein as structure building element, as opposed to non-framework elements which can be present in the pores and/or cavities formed by the CHA framework structure and typical for zeolitic materials in general. Preferred pentavalent elements Z according to the present invention include P, As, Sb, Bi, V, Nb, Ta, and mixtures of two or more thereof. More preferably, Z stands for one or more elements selected from the group consisting of P, As, V, and mixtures of two or more thereof, wherein more preferably Z comprises P or As. According to particularly preferred embodiments thereof, Z comprises P, wherein it is particularly preferred that Z is P.

According to particular embodiments of the present invention, the zeolitic material having a CHA framework structure comprises zeolite crystals having a core-shell structure of which the core-portion displays a diameter of 450 nm or greater. According to the present invention, there is no particular restriction as to the method according to which the dimensions of the core-portion of the zeolite crystals may be determined. It is however preferred according to the present invention that the dimensions of the core portion of the zolite crystals is determined by transmission electron microscopy (TEM). According to the present invention, the diameter of the core-portion of the zeolite crystals generally refers to the largest dimension of said core-portion, wherein according to a preferred meaning of the present invention, the diameter of the core-portion refers to its average diameter, and in particular is equal to the sum of the largest and smallest dimension thereof divided by two, thus giving the average of largest and smallest dimensions. According to a particularly preferred meaning of the present invention, however, the diameter of the seed crystals refers to the smallest dimension of the seed crystal, wherein the dimensions are again preferably those determined by TEM.

Although there is no general limit as to the maximum size or diameter with respect to the diameter which the core-portion of the zeolite crystals display, it is preferred according to the inventive process that the core-portion displays a diameter comprised in the range of from 450 nm to 50 µm, wherein more preferably the diameter of the core-portion of the zeolite crystals is comprised in the range of from 500 nm to 45 µm, more preferably of from 700 nm to 30 µm, more preferably of from 900 nm to 20 µm, more preferably of from 1.1 to 15 µm, more preferably of from 1.5 to 10 µm, more preferably of from 1.8 to 7 µm, more preferably of from 2 to 5 µm, and even more preferably of from 2.3 to 4 µm. According to particularly preferred embodiments of the present invention, the core-portion of the zeolite crystals have a diameter comprised in the range of from 2.5 to 3.5 µm.

Thus, according to the present invention the core-portion displays a diameter comprised in the range of from 450 nm to 50 µm, preferably of from 500 nm to 45 µm, more preferably of from 700 nm to 30 µm, more preferably of from 900 nm to 20 µm, more preferably of from 1.1 to 15 µm, more preferably of from 1.5 to 10 µm, more preferably of from 1.8 to 7 µm, more preferably of from 2 to 5 µm, more preferably of from 2.3 to 4 µm, and even more preferably of from 2.5 to 3.5 µm.

Furthermore, according to embodiments of the present invention, the zeolite crystals having a CHA framework structure have a core-shell structure, wherein the shell-portion comprises $Z_2O_5$ and $X_2O_3$ in the CHA framework structure thereof. As for $YO_2$, $X_2O_3$ and optionally $Z_2O_5$ comprised in the core-portion of the zeolite crystals, $Z_2O_5$ and $X_2O_3$ comprised in the shell portion is contained in the framework structure of the zeolitic material having a CHA framework structure as structure building elements, as opposed to non-framework elements which can be present in the pores and/or cavities formed by the framework structure and typical for zeolitic materials in general.

In principle, the shell-portion of the zeolite crystals having a CHA framework structure comprised in the zeolitic material of the present invention may comprise any conceivable pentavalent element Z, wherein Z stands for either one or several pentavalent elements. Furthermore, the one or more pentavalent element elements Z comprised in the shell-portion of the zeolite crystals may be the same as or different that the one or more pentavalent elements Z optionally comprised in the core-portion, wherein preferably the one or more pentavalent elements Z comprised in the shell-portion are the same as the one of more pentavalent elements Z optionally comprised in the core-portion. Preferred pentavalent elements Z comprised in the shell-portion of the zeolite crystals include P, As, Sb, Bi, V, Nb, Ta, and mixtures of two or more thereof. More preferably, Z stands for one or more elements selected from the group consisting of P, As, V, and mixtures of two or more thereof, wherein more preferably Z comprises P or As. According to particularly preferred embodiments thereof, Z comprises P, wherein it is particularly preferred that Z is P.

Z optionally comprised in the core-portion of the zeolite crystals
and/or (preferably and),
wherein Z comprised in the shell-portion of the zeolite crystals are, independently from one another, selected from the group consisting of P, As, Sb, Bi, V, Nb, Ta, and combinations of two or more thereof, preferably from the group consisting of P, As, V, and combinations of two or more thereof, wherein more preferably Z comprises P or As, preferably P, and wherein even more preferably Z is P.

Furthermore, the shell-portion of the zeolite crystals having a CHA framework structure comprised in the zeolitic material of the present invention may comprise any suitable trivalent element X, wherein again X stands for either one or several trivalent elements. In particular, the one or more trivalent element elements X comprised in the shell-portion of the zeolite crystals may be the same as or different that the one or more trivalent elements X comprised in the core-portion, wherein preferably the one or more trivalent elements X comprised in the shell-portion are the same as the one of more trivalent elements X comprised in the core-portion. Preferred trivalent elements X comprised in the shell-portion of the zeolite crystals include Al, B, In, and Ga, and combinations thereof. More preferably, X stands for Al or Ga. According to particularly preferred embodiments, X comprises Al, wherein it is particularly preferred that X stands for Al.

Thus, according to the present invention, embodiments are preferred wherein X comprised in the core-portion of the zeolite crystals
and/or (preferably and)
wherein X comprised in the shell-portion of the zeolite crystals are, independently from one another, selected from the group consisting of Al, B, In, Ga, and combinations of two or more thereof, wherein X preferably comprises Al or Ga, wherein more preferably X comprises Al, and wherein even more preferably X is Al According to certain embodiments of the present invention, the shell-portion of the zeolite crystals having a CHA framework structure comprised in the zeolitic material of the present invention further comprises $YO_2$, wherein Y stands for any conceivably tetravalent element, Y standing for either one or several tetravalent elements. As defined in the foregoing with respect to $Z_2O_5$ and $X_2O_3$, $YO_2$ which is preferably comprised in the framework structure of the zeolitic material having a CHA framework structure is contained therein as structure building element, as opposed to non-framework elements which can be present in the pores and/or cavities formed by the CHA framework structure and typical for zeolitic materials in general. Furthermore, the one or more tetravalent element elements Y preferably comprised in the shell-portion of the zeolite crystals may be the same as or different that the one or more tetravalent elements Y comprised in the core-portion, wherein preferably the one or more tetravalent elements Y comprised in the shell-portion are the same as the one of more tetravalent elements Y comprised in the core-portion. Preferred tetravalent elements Y comprised in the shell-portion of the zeolite crystals include Si, Sn, Ti, Zr, and Ge, and combinations of two or more thereof. More preferably, Y stands for Si, Ti, or Zr, or any combination of said tetravalent elements, even more preferably for Si and/or Sn. According to the present invention, it is particularly preferred that Y stands for Si.

Therefore, according to the present invention, embodiments are preferred wherein Y comprised in the core-portion of the zeolite crystals and/or (preferably and)
wherein Y preferably comprised in the shell-portion of the zeolite crystals are, independently from one another, selected from the group consisting of Si, Sn, Ti, Zr, Ge, and combinations of two or more thereof, wherein Y preferably comprises Si, and wherein even more preferably Y is Si.

According to particular embodiments of the present invention, the Z:X molar ratio of the zeolite framework structure of the shell-portion of the zeolite crystals comprised in the zeolitic material having a CHA framework structure is greater than the Z:X molar ratio of the zeolite framework structure of the core-portion thereof. Thus, it has surprisingly been found that by providing zeolite crystals having a core-shell structure of which the core-portion displays a Z:X ratio which is lower than the shell-portion thereof, the advantages of the respectively different properties due to the varying composition of the core- and shell-portions may be synergistically combined to afford a novel zeolitic material with unique properties, in particular in catalytic application. Thus, by way of example, it has quite unexpectedly found that the advantages of a core-portion displaying a low Z:X molar ratio as is for example the case in Chabazite which does not contain a pentavalent element in its aluminosilicate framework, may be utilized in catalytic applications such as for example as a catalyst in the methanol to olefin (MTO) process wherein it displays a high activity, without however encountering the disadvantages linked to the use of such a highly active catalyst, in particular in view of the typical coke formation occurring at the catalyst surface and eventually leading to its deactivation. More specifically, it has surprisingly been found that by providing a shell-portion also having the CHA framework structure onto such Chabazite crystals according to the present invention, wherein the shell-portion comprises $Z_2O_5$ and therefore has a higher Z:X molar ratio as the Chabazite core, the activity at the surface of the crystals may be brought to a level at which coking is greatly reduced, as a result of which the catalyst lifetime may be considerably improved. Thus, a zeolitic material is provided wherein the high activity of the core portion of the material may be utilized in a catalytic process, while the shell-portion displays a lower activity due to the higher Z:X molar ratio, thus suppressing undesired side reactions such as coking at the catalyst surface.

Therefore, according to one or more embodiments of the present invention, the Z:X molar ratio of the zeolite framework structure of the shell-portion of the zeolite crystals having a core-shell structure is greater than the Z:X molar ratio of the zeolite framework structure of the core-portion.

In principle, there is no general restriction according to the present invention as to the Z:X molar ratio of the shell-portion of the zeolite crystals. Thus, as concerns the Z:X molar ratio of the shell-portion of the zeolite crystals, the molar ratio may have any suitable value. By way of example, the Z:X molar ratio of the shell-portion may be comprised in the range of anywhere from 0.01 to 20, wherein preferably the Z:X molar ratio of the shell-portion is comprised in the range of from 0.05 to 10, more preferably of from 0.1 to 7, more preferably of from 0.3 to 5, more preferably of from 0.5 to 3, more preferably of from 0.7 to 2, more preferably of from 0.9 to 1.7, and even more preferably of 1.1 to 1.5. According to particularly preferred embodiments of the present invention, the Z:X molar ratio of the shell-portion of the zeolite crystals is comprised in the range of from 1.25 to 1.35.

Furthermore, there is no general restriction according to the present invention as to the value which the ratio of the of the Z:X molar ratio of the shell-portion to the Z:X molar ratio of the core-potion of the zeolite crystals may have, wherein it is preferred that the Z:X molar ratio of the shell-portion is greater than the Z:X molar ratio of the core-portion. Thus, by way of example, the Z:X molar ratio of the zeolite framework structure of the shell-portion of the zeolite crystals may be greater than the Z:X molar ratio of the zeolite framework structure of the core-portion of the zeolite crystals by a factor of 1.5 or more, wherein preferably the Z:X molar ratio of the shell-portion is greater by a factor of 2 or more, more preferably of 5 or more, more preferably of, more preferably of 10 or more, more preferably of 50 or more, more preferably of 100 or more, more preferably of $10^3$ or more, more preferably of $10^4$ or more, more preferably of $10^5$ or more, and even more preferably of $10^6$ or more. According to particularly preferred embodiments of the present invention, the core-portion of the zeolite crystals does not contain $Z_2O_5$ in the zeolite framework structure of said core-portion, such that the Z:X molar ration of the shell-portion which contains $Z_2O_5$ is accordingly infinitely greater than the Z:X molar ratio of the core-portion which is equal to zero.

Thus, according to certain embodiments of the present invention, the Z:X molar ratio of the zeolite framework structure of the shell-portion of the zeolite crystals is greater than the Z:X molar ratio of the zeolite framework structure of the core-portion of the zeolite crystals by a factor of 1.5 or more, preferably by a factor of 2 or more, more preferably of 5 or more, more preferably of, more preferably of 10 or more, more preferably of 50 or more, more preferably of 100 or more, more preferably of $10^3$ or more, more preferably of $10^4$ or more, more preferably of $10^5$ or more, more preferably of $10^6$ or more, and wherein even more preferably the core-portion of the zeolite crystals does not contain $Z_2O_5$ in the zeolite framework structure of said core-portion.

According to the present invention, there is no particular restriction as to the Y:X molar ratio of the core-portion of the zeolite crystals having a CHA framework structure. Thus, by way of example, the Y:X molar ratio of the core-portion may range anywhere from 1 to 100, wherein preferably the Y:X molar ratio of the core portion is comprised in the range of from 5 to 50, more preferably of from 10 to 30, more preferably of from 15 to 20, and even more preferably of from 16 to 18. According to particular preferred embodiments of the present invention, the Y:X molar ratio of the core-portion of the zeolite crystals is comprised in the range of from 16.5 to 17.

As regards embodiments of the present invention wherein the core-portion further comprises $Z_2O_5$ in the framework structure in addition to $YO_2$ and $X_2O_3$, the said core portion accordingly displays a ratio of one or more tetravalent elements Y to one or more trivalent elements X to one or more pentavalent elements Z which may be expressed in terms of a Y:nX:pZ molar ratio, wherein n and p respectively stand for a positive natural number. As for the Y:X molar ratio of in zeolite crystals of the present invention having a core-shell structure which do not further comprise $Z_2O_5$ in the core-portion thereof, there is no particular restriction as to the Y:nX:pZ molar ratio in zeolite crystals of which the core-portion further comprises $Z_2O_5$. According to embodiments of the present invention wherein the core-portion of the zeolite crystals comprise $Z_2O_5$ in their CHA framework structure it is however preferred that the value for the ratio (1+2p):(n−p) is comprised in the range of from 1 to 100, and more preferably in the range of from 5 to 50, more preferably of from 10 to 30, more preferably of from 15 to 20, and even more preferably of from 16 to 18. According to particularly preferred embodiments of the present invention, the ratio (1+2p):(n−p) of the Y:nX:pZ molar ratio of seed crystals having the CHA framework structure further comprising $Z_2O_5$ is comprised in the range of from 16.5 to 17.

Therefore, the present invention includes embodiments wherein the Y:X molar ratio of the zeolite framework structure of the core-portion of the zeolite crystals is comprised in the range of from 1 to 100, preferably of from 5 to 50, more preferably of from 10 to 30, more preferably of from 15 to 20, more preferably of from 16 to 18, and even more preferably of from 16.5 to 17, and wherein if the zeolite framework structure of the core-portion of the zeolite crystals further comprises $Z_2O_5$ in addition to $YO_2$ and $X_2O_3$, the zeolite framework structure of the core-portion displays a Y:nX:pZ molar ratio, wherein the value for the ratio (1+2p):(n−p) is comprised in the range of from 1 to 100, preferably of from 5 to 50, more preferably of from 10 to 30, more preferably of from 15 to 20, more preferably of from 16 to 18, and even more preferably of from 16.5 to 17.

According to the present invention there is no particular restriction as to the type of zeolitic materials which may be comprised in the respective core- and shell-portions of the zeolite crystals having a core-shell structure. Thus, in principle, the core portion may comprise any suitable type of zeolitic material having a CHA framework structure, wherein preferably the zeolitic material of the core-portion comprises one or more zeolites selected from the group consisting of (Ni(deta)$_2$)-UT-6, Chabazite, |Li—Na| [Al—Si—O]-CHA, DAF-5, Dehyd. Na-Chabazite, K-Chabazite (Iran), LZ-218, Linde D, Linde R, MeAPSO-47, Phi, SAPO-34, SAPO-47, SSZ-13, SSZ-62, UiO-21, Willhendersonite, ZK-14, ZYT-6, and combinations of two or more thereof, and wherein more preferably the core-portion comprises one or more zeolites selected from the group consisting of (Ni(deta)$_2$)-UT-6, Chabazite, |Li—Na| [Al—Si—O]-CHA, DAF-5, Dehyd. Na-Chabazite, K-Chabazite (Iran), LZ-218, Linde D, Linde R, Phi, SSZ-13, SSZ-62, UiO-21, Willhendersonite, ZK-14, ZYT-6, and combinations of two or more thereof, wherein even more preferably the core-portion of the zeolite crystals comprises Chabazite and/or SSZ-13. According to particularly preferred embodiments of the present invention, the core-portion of the zeolite crystals comprises Chabazite, wherein even more preferably the core-portion of the zeolite crystals consists of Chabazite.

Thus, the present invention includes embodiments wherein the core-portion of the zeolite crystals comprises one or more zeolites selected from the group consisting of (Ni(deta)$_2$)-UT-6, Chabazite, |Li—Na| [Al—Si—O]-CHA, DAF-5, Dehyd. Na-Chabazite, K-Chabazite (Iran), LZ-218, Linde D, Linde R, MeAPSO-47, Phi, SAPO-34, SAPO-47, SSZ-13, SSZ-62, UiO-21, Willhendersonite, ZK-14, ZYT-6, and combinations of two or more thereof, preferably from the group consisting of (Ni(deta)$_2$)-UT-6, Chabazite, |Li—Na| [Al—Si—O]-CHA, DAF-5, Dehyd. Na-Chabazite, K-Chabazite (Iran), LZ-218, Linde D, Linde R, Phi, SSZ-13, SSZ-62, UiO-21, Willhendersonite, ZK-14, ZYT-6, and combinations of two or more thereof, and wherein even more preferably the core-portion of the zeolite crystals comprises Chabazite and/or SSZ-13, preferably Chabazite preferred.

Furthermore, as regards the shell-portion of the zeolite crystals having a core-shell structure, said portion may accordingly also comprise any suitable type of zeolitic material having a CHA framework structure. Preferably the zeolitic material of the shell-portion of the zeolite crystals comprises one or more zeolites selected from the group consisting of [Al—As—O]-CHA, [Al—Co—P—O]-CHA, [Co—Al—P—O]-CHA, [Mg—Al—P—O]-CHA, [Zn—Al—P—O]-CHA, AlPO-34, CoAPO-44, CoAPO-47, GaPO-34, MeAPO-47, MeAPSO-47, SAPO-34, SAPO-47, ZYT-6, and combinations of two or more thereof, wherein more preferably the shell-portion comprises one or more zeolites selected from the group consisting of MeAPSO-47, SAPO-34, SAPO-47, ZYT-6, and combinations of two or more thereof. According to particularly preferred embodiments of the present invention, the shell-portion of the zeolite crystals comprises SAPO-34, wherein even more preferably the shell-portion of the zeolite crystals consists of SAPO-34.

Therefore, embodiments are further preferred according to the present invention wherein the shell-portion of the zeolite crystals comprises one or more zeolites selected from the group consisting of [Al—As—O]-CHA, [Al—Co—P—O]-CHA, [Co—Al—P—O]-CHA, [Mg—Al—P—O]-CHA, [Zn—Al—P—O]-CHA, AlPO-34, CoAPO-44, CoAPO-47, GaPO-34, MeAPO-47, MeAPSO-47, SAPO-34, SAPO-47, ZYT-6, and combinations of two or more thereof, preferably from the group consisting of MeAPSO-47, SAPO-34, SAPO-47, ZYT-6, and combinations of two or more thereof, wherein even more preferably the shell-portion of the zeolite crystals comprise SAPO-34.

As for microporous materials in general, the zeolitic material of the present invention may also be characterized by its surface area. In this respect, there is no particular restriction according to the present invention as to the surface area which the zeolitic material having a CHA framework structure may have, in particular with respect to the zeolite crystals having a core-shell structure. Thus, by way of example, the BET surface area of the zeolitic material having a CHA framework structure and in particular of the zeolite crystals having a core-shell structure as determined according to DIN 66135 may range anywhere from 250 to 750 $m^2/g$. Preferably the BET surface area determined according to DIN 66135 is comprised in the range of from 400 to 700 $m^2/g$, and even more preferably in the range of from 500 to 650 $m^2/g$. According to particularly preferred embodiments of the present invention the BET surface area of the zeolitic material having a CHA framework structure is comprised in the range of from 550 to 600 $m^2/g$.

Depending on the specific needs of its application, the zeolitic material of the present invention can be employed as such, like in the form of a powder, a spray powder or a spray granulate obtained from above-described separation techniques, e.g. decantation, filtration, centrifugation, or spraying.

In many industrial applications, it is often desired on the part of the user not to employ the zeolitic material as powder or sprayed material, i.e. the zeolitic material obtained by the separation of the material from its mother liquor, optionally including washing and drying, and subsequent calcination, but a zeolitic material which is further processed to give moldings. Such moldings are required particularly in many industrial processes, e.g. in many processes wherein the zeolitic material of the present invention is employed as catalyst or adsorbent.

Accordingly, the present invention also relates to a molding comprising the inventive zeolitic material.

In general, the powder or sprayed material can be shaped without any other compounds, e.g. by suitable compacting, to obtain moldings of a desired geometry, e.g. tablets, cylinders, spheres, or the like.

Generally, the powder or sprayed material is admixed with or coated by a suitable refractory binder. In general, suitable binders are all compounds which impart adhesion and/or cohesion between the zeolitic material particles to be bonded which goes beyond the physisorption which may be present without a binder. Examples of such binders are metal oxides, such as, for example, $SiO_2$, $Al_2O_3$, $TiO_2$, $ZrO_2$ or MgO or clays, or mixtures of two or more of these compounds. Naturally occurring clays which can be employed include the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification. In addition, the zeolitic material according to the present invention can be composited with a porous matrix material such as silica-alumina, silica-magnesia, silica-zirconia, silica-thoria, silica-beryllia and silica-titania as well as ternary compositions such as silica-alumina-thoria, silica-alumina-zirconia, silica-alumina-magnesia and silica-magnesia-zirconia.

The zeolitic material of the present invention may therefore also be provided in the form of extrudates, pellets, tablets or particles of any other suitable shape, for use as a packed bed of particulate catalyst, or as shaped pieces such as plates, saddles, tubes, or the like.

In general, the powder or the sprayed material, optionally after admixing or coating by a suitable refractory binder as described above, is formed into a slurry, for example with water, which is deposited upon a suitable refractory carrier. The slurry may also comprise other compounds such as, e.g., stabilizers, defoamers, promoters, or the like. Typically, the carrier comprises a member, often referred to as a "honeycomb" carrier, comprising one or more refractory bodies having a plurality of fine, parallel gas flow passages extending there through. Such carriers are well known in the art and may be made of any suitable material such as cordierite or the like.

In general, the zeolitic material described above can be used as molecular sieve, adsorbent, catalyst, catalyst support or binder thereof. For example, the zeolitic material can be used as molecular sieve to dry gases or liquids, for selective molecular separation, e.g. for the separation of hydrocarbons or amides; as ion exchanger; as chemical carrier; as adsorbent, in particular as adsorbent for the separation of hydrocarbons or amides; or as a catalyst. Most preferably, the zeolitic material according to the present invention is used as a catalyst and/or as a catalyst support.

According to a particular embodiment of the present invention, the zeolitic material of the invention is used in a catalytic process, preferably as a catalyst and/or catalyst support, and more preferably as a catalyst. In general, the zeolitic material of the invention can be used as a catalyst and/or catalyst support in any conceivable catalytic process, wherein processes involving the conversion of at least one organic compound is preferred, more preferably of organic compounds comprising at least one carbon-carbon and/or carbon-oxygen and/or carbon-nitrogen bond, more preferably of organic compounds comprising at least one carbon-carbon and/or carbon-oxygen bond, and even more preferably of organic compounds comprising at least one carbon-carbon bond. In particularly preferred embodiments of the present invention, the zeolitic material is used as a catalyst and/or catalyst support in a fluid catalytic cracking (FCC) process.

Furthermore, the zeolitic material according to the invention may be used as a catalyst for producing light olefins from non-petroleum feedstock by conversion of oxygenates, such as lower alcohols (methanol, ethanol), ethers (dimethyl ether, methyl ethyl ether), esters (dimethyl carbonate, methyl formate) and the like to olefins, and especially in the conversion of lower alcohols to light olefins. According to particularly preferred embodiments, the zeolitic material of the present invention is used in the conversion of methanol to olefin (MTO)

According to a further embodiment of the present invention, the zeolitic material of the invention is used in a catalytic process involving the conversion of at least one compound comprising at least one nitrogen-oxygen bond. Particularly preferred according to the present invention is the use of the zeolitic material as a catalyst and/or catalyst support in a selective catalytic reduction (SCR) process for the selective reduction of nitrogen oxides $NO_x$; for the oxidation of $NH_3$, in particular for the oxidation of $NH_3$ slip in diesel systems; for the decomposition of $N_2O$. The term nitrogen oxides, $NO_x$, as used in the context of the present invention designates the oxides of nitrogen, especially dinitrogen oxide ($N_2O$), nitrogen monoxide (NO), dinitrogen trioxide ($N_2O_3$), nitrogen dioxide ($NO_2$), dinitrogen tetroxide ($N_2O_4$), dinitrogen pentoxide ($N_2O_5$), nitrogen peroxide ($NO_3$). According to particularly preferred embodiments of the present invention, the zeolitic material used in a catalytic process involving the conversion of at least one compound comprising at least one nitrogen-oxygen bond comprises Cu and/or Fe, and more preferably Cu.

Therefore, the present invention also relates to a method for selectively reducing nitrogen oxides $NO_x$ by contacting a stream containing $NO_x$ with a catalyst containing the zeolitic material according to the present invention under suitable reducing conditions; to a method of oxidizing $NH_3$, in particular of oxidizing $NH_3$ slip in diesel systems, by contacting a stream containing $NH_3$ with a catalyst containing the zeolitic material according to the present invention under suitable oxidizing conditions; to a method of decomposing of $N_2O$ by contacting a stream containing $N_2O$ with a catalyst containing the zeolitic material according to the present invention under suitable decomposition conditions; to a method of controlling emissions in Advanced Emission Systems such as Homogeneous Charge Compression Ignition (HCCI) engines by contacting an emission stream with a catalyst containing the zeolitic material according to the present invention under suitable conditions; to a fluid catalytic cracking FCC process wherein the zeolitic material according to the present invention is employed as additive; to a method of converting an organic compound by contacting said compound with a catalyst containing the zeolitic material according to the present invention under suitable conversion conditions; to a "stationary source" process wherein a catalyst is employed containing the zeolitic material according to the present invention.

Therefore, the present invention also relates to a method for selectively reducing nitrogen oxides $NO_x$, wherein a gaseous stream containing nitrogen oxides $NO_x$, preferably also containing ammonia and/urea, is contacted with the zeolitic material according to the present invention or the zeolitic material obtainable or obtained according to the present invention, preferably in the form of a molded catalyst, still more preferably as a molded catalyst wherein the zeolitic material is deposited on a suitable refractory carrier, still more preferably on a "honeycomb" carrier.

The nitrogen oxides which are reduced using a catalyst containing the zeolitic material according to the present invention or the zeolitic material obtainable or obtained according to the present invention may be obtained by any process, e.g. as a waste gas stream. Among others, waste gas streams as obtained in processes for producing adipic acid, nitric acid, hydroxylamine derivatives, caprolactame, glyoxal, methyl-glyoxal, glyoxylic acid or in processes for burning nitrogenous materials may be mentioned.

In specific embodiments, the zeolitic material according to the present invention or the zeolitic material obtainable or obtained according to the present invention is used as a molded catalyst, still more preferably as a molded catalyst wherein the zeolitic material is deposited on a suitable refractory carrier, still more preferably on a "honeycomb" carrier, for the selective reduction of nitrogen oxides $NO_x$, i.e. for selective catalytic reduction of nitrogen oxides. In particular, the selective reduction of nitrogen oxides wherein the zeolitic material according to the present invention is employed as catalytically active material is carried out in the presence ammonia or urea. While ammonia is the reducing agent of choice for stationary power plants, urea is the reducing agent of choice for mobile SCR systems. Typically, the SCR system is integrated in the engine and vehicle design and, also typically, contains the following main components: SCR catalyst containing the zeolitic material according to the present invention; a urea storage tank; a urea pump; a urea dosing system; a urea injector/nozzle; and a respective control unit.

Furthermore, in specific embodiments according to the present invention that the zeolitic material is used as a molecular trap for organic compounds. In general, any type of organic compound may be trapped in the zeolitic material, wherein it is preferred that the compound is reversibly trapped, such that it may be later released from the zeolitic material, preferably wherein the organic compound is released—preferably without conversion thereof—by an increase in temperature and/or a decrease in pressure. Furthermore, it is preferred that the zeolitic material is used to trap organic compounds of which the dimensions allow them to penetrate the microporous system of the molecular structure. According to yet further embodiments of the present invention, it is preferred that the trapped compounds are released under at least partial conversion thereof to a chemical derivative and/or to a decomposition product thereof, preferably to a thermal decomposition product thereof.

When preparing specific catalytic compositions or compositions for different purposes, it is also conceivable to blend the zeolitic material according to the present invention with at least one other catalytically active material or a material being active with respect to the intended purpose. It is also possible to blend at least two different inventive materials which may differ in the $YO_2:X_2O_3$ ratio, preferably in the $SiO_2:Al_2O_3$ ratio, and/or in the presence or absence of one or more further metals such as one or more transition metals and/or in the specific amounts of a further metal such as a transition metal, wherein according to particularly preferred embodiments, the one or more transition metal comprises Cu and/or Fe, more preferably Cu. It is also possible to blend at least two different inventive materials with at least one other catalytically active material or a material being active with respect to the intended purpose.

Also, the catalyst may be disposed on a substrate. The substrate may be any of those materials typically used for preparing catalysts, and will usually comprise a ceramic or metal honeycomb structure. Any suitable substrate may be employed, such as a monolithic substrate of the type having fine, parallel gas flow passages extending there through from an inlet or an outlet face of the substrate, such that passages are open to fluid flow there through (referred to as honeycomb flow through substrates). The passages, which are essentially straight paths from their fluid inlet to their fluid outlet, are defined by walls on which the catalytic material is disposed as a washcoat so that the gases flowing through the passages contact the catalytic material. The flow passages of the monolithic substrate are thin-walled channels, which can be of any suitable cross-sectional shape and size such as trapezoidal, rectangular, square, sinusoidal, hexagonal, oval, circular, etc. Such structures may contain from about 60 to about 400 or more gas inlet openings (i.e., cells) per square inch (2.54 cm×2.54 cm) of cross section.

The substrate can also be a wall-flow filter substrate, where the channels are alternately blocked, allowing a gaseous stream entering the channels from one direction (inlet direction), to flow through the channel walls and exit from the channels from the other direction (outlet direction). The catalyst composition can be coated on the flow through or wall-flow filter. If a wall flow substrate is utilized, the resulting system will be able to remove particulate matter along with gaseous pollutants. The wall-flow filter substrate can be made from materials commonly known in the art, such as cordierite, aluminum titanate or silicon carbide. It will be understood that the loading of the catalytic composition on a wall flow substrate will depend on substrate properties such as porosity and wall thickness, and typically will be lower than loading on a flow through substrate.

The ceramic substrate may be made of any suitable refractory material, e.g., cordierite, cordierite-alumina, silicon nitride, zircon mullite, spodumene, alumina-silica magnesia, zircon silicate, sillimanite, a magnesium silicate, zircon, petalite, alpha-alumina, an aluminosilicate, and the like.

The substrates useful for the catalysts of embodiments of the present invention may also be metallic in nature and be composed of one or more metals or metal alloys. The metallic substrates may be employed in various shapes such as corrugated sheet or monolithic form. Suitable metallic supports include the heat resistant metals and metal alloys such as titanium and stainless steel as well as other alloys in which iron is a substantial or major component. Such alloys may contain one or more of nickel, chromium and/or aluminum, and the total amount of these metals may advantageously comprise at least 15 wt. % of the alloy, e.g., 10-25 wt. % of chromium, 3-8 wt. % of aluminum and up to 20 wt. % of nickel. The alloys may also contain small or trace amounts of one or more other metals such as manganese, copper, vanadium, titanium, and the like. The surface or the metal substrates may be oxidized at high temperatures, e.g., 1000° C. and higher, to improve the resistance to corrosion of the alloys by forming an oxide layer on the surfaces of the substrates. Such high temperature-induced oxidation may enhance the adherence of the refractory metal oxide support and catalytically promoting metal components to the substrate.

In alternative embodiments, zeolitic material according to the present invention may be deposited on an open cell foam substrate. Such substrates are well known in the art, and are typically formed of refractory ceramic or metallic materials.

Especially preferred is the use of a catalyst containing the zeolitic material according to the present invention or the zeolitic material obtainable or obtained according to the present invention for removal of nitrogen oxides $NO_x$ from exhaust gases of internal combustion engines, in particular diesel engines, which operate at combustion conditions with air in excess of that required for stoichiometric combustion, i.e., lean.

Therefore, the present invention also relates to a method for removing nitrogen oxides NO from exhaust gases of internal combustion engines, in particular diesel engines, which operate at combustion conditions with air in excess of that required for stoichiometric combustion, i.e., at lean conditions, wherein a catalyst containing the zeolitic material according to the present invention or the zeolitic material obtainable or obtained according to the present invention is employed as catalytically active material.

The present invention therefore relates to the use of the zeolitic material of the invention, in particular in the field of catalysis and/or in the treatment of exhaust gas, wherein said exhaust gas treatment comprises industrial and automotive exhaust gas treatment. In these and other applications, the zeolitic material of the present invention can by way of example be used as a molecular sieve, catalyst, and/or catalyst support.

In embodiments of the present invention involving the use of the zeolitic material of the invention in exhaust gas treatment, the zeolitic material is preferably used in the treatment of industrial or automotive exhaust gas, more preferably as a molecular sieve in said applications. In a particularly preferred embodiment, the zeolitic material used in exhaust gas treatment is comprised in a hydrocarbon trap.

Therefore, the present invention further relates to the use of a zeolitic material according to the present invention, and in particular according to preferred and particularly preferred embodiments thereof as defined in the present application, as a molecular sieve, as an adsorbent, for ion-exchange, as a catalyst and/or as a catalyst support, preferably as a catalyst for the selective catalytic reduction (SCR) of nitrogen oxides $NO_x$; for the oxidation of $NH_3$, in particular for the oxidation of $NH_3$ slip in diesel systems; for the decomposition of $N_2O$; as an additive in fluid catalytic cracking (FCC) processes; and/or as a catalyst in organic conversion reactions, preferably in the conversion of alcohols to olefins, and more preferably in methanol to olefin (MTO) catalysis.

The present invention is further characterized by the following embodiments, wherein these include the specific combinations of embodiments as indicated by the respective dependencies defined therein:

1. A process for the preparation of a zeolitic material having a CHA framework structure, said zeolitic material comprising zeolite crystals having a core-shell structure, wherein said process comprises the steps of
   (1) providing a mixture comprising one or more sources for $Z_2O_5$, one or more sources for $X_2O_3$, optionally one or more structure directing agents, and seed crystals having a CHA framework structure, wherein the CHA framework structure of the seed crystals comprises $YO_2$, $X_2O_3$, and optionally $Z_2O_5$, and wherein the seed crystals have a diameter of 450 nm or greater;
   (2) crystallizing the mixture provided in (1) to afford zeolite crystals comprising a core of seed crystal provided in step (1) and a shell crystallized on the seed crystal;
   wherein Z is a pentavalent element, Y is a tetravalent element, and X is a trivalent element, and
   wherein preferably one or more sources for $YO_2$ are further provided in step (1).

2. The process of embodiment 1, wherein the seed crystals have a diameter comprised in the range of from 450 nm to 50 μm, preferably of from 500 nm to 45 μm, more preferably of from 700 nm to 30 μm, more preferably of from 900 nm to 20 μm, more preferably of from 1.1 to 15 μm, more preferably of from 1.5 to 10 μm, more preferably of from 1.8 to 7 μm, more preferably of from 2 to 5 μm, more preferably of from 2.3 to 4 μm, and even more preferably of from 2.5 to 3.5 μm.

3. The process according to embodiment 1 or 2, wherein the CHA framework structure of the seed crystals displays a Y:X molar ratio comprised in the range of from 1 to 100, preferably of from 5 to 50, more preferably of from 10 to 30, more preferably of from 15 to 20, more preferably of from 16 to 18, and even more preferably of from 16.5 to 17, and
   wherein if the CHA framework structure of the seed crystals further comprises $Z_2O_5$ in addition to $YO_2$ and $X_2O_3$, the seed crystals display a Y:nX:pZ molar ratio,
   wherein the value for the ratio $(1+2p):(n-p)$ is comprised in the range of from 1 to 100, preferably of from 5 to 50, more preferably of from 10 to 30, more preferably of from 15 to 20, more preferably of from 16 to 18, and even more preferably of from 16.5 to 17.

4. The process according to any of embodiments 1 to 3, wherein Y comprised in the seed crystals
   and/or, preferably and,
   wherein Y preferably further provided in step (1) in the one or more sources for $YO_2$ are, independently from one another, selected from the group consisting of Si, Sn, Ti, Zr, Ge, and combinations of two or more thereof, wherein Y preferably comprises Si, and wherein even more preferably Y is Si.

5. The process according to any of embodiments 1 to 4, wherein X comprised in the seed crystals
   and/or, preferably and,
   wherein X provided in step (1) in the one or more sources for $X_2O_3$ are, independently from one another, selected from the group consisting of Al, B, In, Ga, and combinations of two or more thereof, wherein X preferably comprises Al or Ga, wherein more preferably X comprises Al, and wherein even more preferably X is Al.

6. The process according to any of embodiments 1 to 5, wherein Z optionally comprised in the seed crystals and/or, preferably and,
wherein Z provided in step (1) in the one or more sources for $Z_2O_5$ are, independently from one another, selected from the group consisting of P, As, Sb, Bi, V, Nb, Ta, and combinations of two or more thereof, preferably from the group consisting of P, As, V, and combinations of two or more thereof, wherein more preferably Z comprises P or As, preferably P, and wherein even more preferably Z is P.

7. The process according to any of embodiments 1 to 6, wherein the seed crystals comprise one or more zeolites selected from the group consisting of (Ni(deta)$_2$)-UT-6, Chabazite, |Li—Na| [Al—Si—O]-CHA, DAF-5, Dehyd. Na-Chabazite, K-Chabazite (Iran), LZ-218, Linde D, Linde R, MeAPSO-47, Phi, SAPO-34, SAPO-47, SSZ-13, SSZ-62, UiO-21, Willhendersonite, ZK-14, ZYT-6, and combinations of two or more thereof, preferably from the group consisting of (Ni(deta)$_2$)-UT-6, Chabazite, |Li—Na| [Al—Si—O]-CHA, DAF-5, Dehyd. Na-Chabazite, K-Chabazite (Iran), LZ-218, Linde D, Linde R, Phi, SSZ-13, SSZ-62, UiO-21, Willhendersonite, ZK-14, ZYT-6, and combinations of two or more thereof, and
wherein even more preferably the seed crystals comprise SSZ-13.

8. The process according to any of embodiments 1 to 7, wherein the one or more sources for $Z_2O_5$ comprises one or more phosphates and/or one or more oxides and/or one or more acids of phosphorous, preferably one or more acids of phosphorous, more preferably phosphoric acid, and wherein even more preferably the source for $Z_2O_5$ is phosphoric acid.

9. The process according to any of embodiments 1 to 8, wherein the one or more sources for $X_2O_3$ comprises one or more compounds selected from the group consisting of aluminate salts, aluminum hydroxides, aluminum oxide hydroxides, and mixtures of two or more thereof, preferably from the group consisting of aluminum hydroxides, aluminum oxide hydroxides, and mixtures of two or more thereof, wherein more preferably the one or more sources for $X_2O_3$ comprises one or more aluminum oxide hydroxides, preferably boehmite and/or diaspore, and more preferably boehmite, and wherein even more preferably the source for $X_2O_3$ is boehmite.

10. The process according to any of embodiments 1 to 9, wherein the one or more sources for $YO_2$ comprises one or more compounds selected from the group consisting of silicas, silicates, and mixtures of two or more thereof, wherein preferably the one or more sources for $YO_2$ comprise one or more silicas, wherein more preferably the one or more sources for $YO_2$ comprise fumed silica, and wherein even more preferably the source for $YO_2$ is fumed silica.

11. The process according to any of embodiments 1 to 10, wherein the $X_2O_3:Z_2O_5$ molar ratio of the mixture provided in step (1) is comprised in the range of 1:(0.05-30), preferably 1:(0.1-15), more preferably 1:(0.2-10), more preferably 1:(0.5-5), more preferably 1:(0.8-3), and even more preferably 1:(1-2.5), and wherein if the mixture provided in step (1) further comprises $YO_2$, the $YO_2:X_2O_3:Z_2O_5$ molar ratio of the mixture provided in step (1) is comprised in the range of (0.01-10):1:(0.05-30), preferably (0.05-5):1:(0.1-15), more preferably (0.1-2):1:(0.2-10), more preferably (0.3-1):1:(0.5-5), more preferably (0.5-0.7):1:(0.8-3), and even more preferably (0.55-0.65):1:(1-2.5).

12. The process according to any of embodiments 1 to 11, wherein the amount of seed crystals in the mixture provided in step (1) ranges from 1-90 wt.-% based on 100 wt.-% of the total amount of $X_2O_3$, $Z_2O_5$, and optional $YO_2$ respectively comprised in the one or more sources for $X_2O_3$, $Z_2O_5$, and optionally preferred $YO_2$, preferably from 3-70 wt.-%, more preferably from 5-50 wt.-%, more preferably from 6-30 wt.-%, more preferably from 7-15 wt.-%, more preferably from 8-12 wt.-%, and even more preferably from 9-11 wt.-%.

13. The process according to any of embodiments 1 to 12, wherein the mixture provided in step (1) further comprises a solvent, wherein said solvent preferably comprises water, more preferably distilled water, wherein even more preferably the solvent is water, preferably distilled water.

14. The process according to any of embodiment 13, wherein the $H_2O:Z_2O_5$ molar ratio of the mixture according to step (1) ranges from 5-100, preferably from 10-70, more preferably from 15-50, more preferably from 20-45, and even more preferably from 23-41, and/or, preferably and,
wherein the $H_2O:X_2O_3$ molar ratio of the mixture according to step (1) ranges from 5-150, preferably from 10-100, more preferably from 30-70, more preferably from 35-60, and even more preferably from 40-53.

15. The process according to any of embodiments 1 to 14, wherein the crystallization in step (2) involves heating of the mixture, preferably at a temperature ranging from 80 to 270° C., more preferably from 100 to 250° C., more preferably from 130 to 240° C., more preferably from 150 to 230° C., more preferably from 180 to 220° C., more preferably from 190 to 210° C., and even more preferably from 195 to 205° C.

16. The process of embodiment 15, wherein the heating in step (2) is conducted under autogenous pressure, preferably under solvothermal conditions, and more preferably under hydrothermal conditions.

17. The process of embodiment 15 or 16, wherein the crystallization in step (2) involves the heating of the mixture for a period ranging from 1 to 50 h, preferably from 1.5 to 30 h, more preferably from 1.5 to 20 h, more preferably from 2 to 13 h, more preferably from 2 to 9 h, more preferably from 2 to 6 h, more preferably from 2 to 4 h, and even more preferably from 2.5 to 3.5 h.

18. The process according to any of embodiments 1 to 17, wherein the structure directing agent comprises one or more compounds selected from the group consisting of tetraalkylammonium compounds, dialkyl amines, heterocyclic amines, and combinations of two or more thereof, preferably from the group consisting of tetra ($C_1$-$C_5$)alkylammonium compounds, di($C_1$-$C_5$)alkyl amines, oxygen containing heteroxyclic amines with 5 to 8 ring members, and combinations of two or more thereof, more preferably from the group consisting of tetra($C_2$-$C_4$)alkylammonium compounds, di($C_2$-$C_4$) alkyl amines, oxygen containing heteroxyclic amines with 5 to 7 ring members, and combinations of two or more thereof, more preferably from the group consisting of tetra($C_2$-$C_3$)alkylammonium compounds, di($C_2$-$C_3$)

alkyl amines, oxygen containing heteroxyclic amines with 5 or 6 ring members, and combinations of two or more thereof, wherein more preferably the structure directing agent comprises one or more compounds selected from the group consisting of tetraethylammonium salts, preferably tetraethylammonium hydroxide, diethyl amine, isopropylamine, di-n-propylamine, morpholine, and combinations of two or more thereof, and wherein even more preferably the structure directing agent comprises diethyl amine and/or morpholine, the structure directing agent preferably being diethyl amine and/or morpholine.

19. The process according to any of embodiments 1 to 18, wherein the zeolitic material having a CHA framework structure crystallized in step (2) comprises one or more zeolites selected from the group consisting of [Al—As—O]-CHA, [Al—Co—P—O]-CHA, [Co—Al—P—O]-CHA, [Mg—Al—P—O]-CHA, [Zn—Al—P—O]-CHA, AlPO-34, CoAPO-44, CoAPO-47, GaPO-34, MeAPO-47, MeAPSO-47, SAPO-34, SAPO-47, ZYT-6, and combinations of two or more thereof,
preferably from the group consisting of MeAPSO-47, SAPO-34, SAPO-47, ZYT-6, and combinations of two or more thereof,
wherein even more preferably the shell-portion of the zeolite crystals comprise SAPO-34.

20. A zeolitic material having a CHA framework structure obtainable and/or obtained, preferably obtained, according to the process of any of embodiments 1 to 19.

21. A zeolitic material having a CHA framework structure, said zeolitic material comprising zeolite crystals having a core-shell structure, wherein
the core-portion of the zeolite crystals comprises $YO_2$, $X_2O_3$, and optionally $Z_2O_5$ in the zeolite framework structure of said core-portion, and wherein
the shell-portion of the zeolite crystals comprises $Z_2O_5$ and $X_2O_3$ in the zeolite framework structure of said shell-portion,
wherein Y is a tetravalent element, X is a trivalent element, and Z is a pentavalent element,
wherein the shell-portion preferably further comprises $YO_2$ in the zeolite framework structure of said shell-portion, and
wherein the core-portion displays a diameter of 450 nm or greater.

22. The zeolitic material of embodiment 21, wherein the core-portion displays a diameter comprised in the range of from 450 nm to 50 µm, preferably of from 500 nm to 45 µm, more preferably of from 700 nm to 30 µm, more preferably of from 900 nm to 20 µm, more preferably of from 1.1 to 15 µm, more preferably of from 1.5 to 10 µm, more preferably of from 1.8 to 7 µm, more preferably of from 2 to 5 µm, more preferably of from 2.3 to 4 µm, and even more preferably of from 2.5 to 3.5 µm.

23. The zeolitic material of embodiment 21 or 22, wherein the Z:X molar ratio of the zeolite framework structure of the shell-portion is greater than the Z:X molar ratio of the zeolite framework structure of the core-portion.

24. The zeolitic material of embodiment 23, wherein the Z:X molar ratio of the zeolite framework structure of the shell-portion of the zeolite crystals is greater than the Z:X molar ratio of the zeolite framework structure of the core-portion of the zeolite crystals by a factor of 1.5 or more, preferably by a factor of 2 or more, more preferably of 5 or more, more preferably of, more preferably of 10 or more, more preferably of 50 or more, more preferably of 100 or more, more preferably of $10^3$ or more, more preferably of $10^4$ or more, more preferably of $10^5$ or more, more preferably of $10^6$ or more, and wherein even more preferably the core-portion of the zeolite crystals does not contain $Z_2O_5$ in the zeolite framework structure of said core-portion.

25. The zeolitic material of any of embodiments 21 to 24, wherein the Z:X molar ratio of the zeolite framework structure of the shell-portion of the zeolite crystals is comprised in the range of from 0.01 to 20, preferably of from 0.05 to 10, more preferably of from 0.1 to 7, more preferably of from 0.3 to 5, more preferably of from 0.5 to 3, more preferably of from 0.7 to 2, more preferably of from 0.9 to 1.7, more preferably of 1.1 to 1.5, and even more preferably of from 1.25 to 1.35.

26. The zeolitic material of any of embodiments 21 to 25, wherein the Y:X molar ratio of the zeolite framework structure of the core-portion of the zeolite crystals is comprised in the range of from 1 to 100, preferably of from 5 to 50, more preferably of from 10 to 30, more preferably of from 15 to 20, more preferably of from 16 to 18, and even more preferably of from 16.5 to 17, and
wherein if the zeolite framework structure of the core-portion of the zeolite crystals further comprises $Z_2O_5$ in addition to $YO_2$ and $X_2O_3$, the zeolite framework structure of the core-portion displays a Y:nX:pZ molar ratio, wherein the value for the ratio $(1+2p):(n-p)$ is comprised in the range of from 1 to 100, preferably of from 5 to 50, more preferably of from 10 to 30, more preferably of from 15 to 20, more preferably of from 16 to 18, and even more preferably of from 16.5 to 17.

27. The zeolitic material of any of embodiments 21 to 26, wherein Y comprised in the core-portion of the zeolite crystals
and/or, preferably and,
wherein Y preferably comprised in the shell-portion of the zeolite crystals are, independently from one another, selected from the group consisting of Si, Sn, Ti, Zr, Ge, and combinations of two or more thereof, wherein Y preferably comprises Si, and wherein even more preferably Y is Si.

28. The zeolitic material of any of embodiments 21 to 27, wherein X comprised in the core-portion of the zeolite crystals
and/or, preferably and,
wherein X comprised in the shell-portion of the zeolite crystals are, independently from one another, selected from the group consisting of Al, B, In, Ga, and combinations of two or more thereof, wherein X preferably comprises Al or Ga, wherein more preferably X comprises Al, and wherein even more preferably X is Al.

29. The zeolitic material of any of embodiments 21 to 28, wherein Z optionally comprised in the core-portion of the zeolite crystals
and/or, preferably and,
wherein Z comprised in the shell-portion of the zeolite crystals are, independently from one another, selected from the group consisting of P, As, Sb, Bi, V, Nb, Ta, and combinations of two or more thereof, preferably from the group consisting of P, As, V, and combinations of two or more thereof, wherein more preferably Z comprises P or As, preferably P, and wherein even more preferably Z is P.

30. The zeolitic material of any of embodiments 21 to 29, wherein the core-portion of the zeolite crystals comprises one or more zeolites selected from the group consisting of (Ni(deta)$_2$)-UT-6, Chabazite, |Li—Na| [Al—Si—O]-CHA, DAF-5, Dehyd. Na-Chabazite, K-Chabazite (Iran), LZ-218, Linde D, Linde R, MeAPSO-47, Phi, SAPO-34, SAPO-47, SSZ-13, SSZ-62, UiO-21, Willhendersonite, ZK-14, ZYT-6, and combinations of two or more thereof, preferably from the group consisting of (Ni(deta)$_2$)-UT-6, Chabazite, |Li—Na| [Al—Si—O]-CHA, DAF-5, Dehyd. Na-Chabazite, K-Chabazite (Iran), LZ-218, Linde D, Linde R, Phi, SSZ-13, SSZ-62, UiO-21, Willhendersonite, ZK-14, ZYT-6, and combinations of two or more thereof, and wherein even more preferably the core-portion of the zeolite crystals comprises Chabazite and/or SSZ-13, preferably Chabazite.

31. The zeolitic material of any of embodiments 21 to 30, wherein the shell-portion of the zeolite crystals comprises one or more zeolites selected from the group consisting of [Al—As—O]-CHA, [Al—Co—P—O]-CHA, [Co—Al—P—O]-CHA, [Mg—Al—P—O]-CHA, [Zn—Al—P—O]-CHA, AlPO-34, CoAPO-44, CoAPO-47, GaPO-34, MeAPO-47, MeAPSO-47, SAPO-34, SAPO-47, ZYT-6, and combinations of two or more thereof, preferably from the group consisting of MeAPSO-47, SAPO-34, SAPO-47, ZYT-6, and combinations of two or more thereof, wherein even more preferably the shell-portion of the zeolite crystals comprise SAPO-34.

32. The zeolitic material of any of embodiments 21 to 31, wherein the BET surface area of the zeolitic material determined according to DIN 66135 ranges from 250 to 750 m$^2$/g, preferably from 400 to 700 m$^2$/g, more preferably from 500 to 650 m$^2$/g, and even more preferably from 550 to 600 m$^2$/g.

33. Use of a zeolitic material having a CHA framework structure according to any of embodiments 20 to 32 as a molecular sieve, as an adsorbent, for ion-exchange, as a catalyst and/or as a catalyst support, preferably as a catalyst for the selective catalytic reduction (SCR) of nitrogen oxides NO$_x$; for the oxidation of NH$_3$, in particular for the oxidation of NH$_3$ slip in diesel systems; for the decomposition of N$_2$O; as an additive in fluid catalytic cracking (FCC) processes; and/or as a catalyst in organic conversion reactions, preferably in the conversion of alcohols to olefins, and more preferably in methanol to olefin (MTO) catalysis.

EXAMPLES

Example 1

Preparation of the Chabazite Seed Crystals 38.95 kg of a trimethyl-1-adamantylammonium hydroxide solution (TMAA, 13.4 wt.-% in water) were placed in an autoclave. Subsequently, 2.65 kg of a 50% sodium hydroxide solution were added and the resulting mixture stirred until the solution was clear. 4.26 kg aluminum triisopropoxide (ATIP, Aldrich) were then added within 5-15 minutes, and stirring was continued for about 2 hours until the solids were reacted and the solution was a uniform suspension. Subsequently, 50 kg Ludox AS-40 were added while stirring to obtain a composition having molar ratios of 36 SiO$_2$:1.1 Al$_2$O$_3$:2.6 TMAA:1.8 Na$_2$O:377H$_2$O.

The autoclave was then sealed and heated to a temperature of 170° C. and maintained at that temperature for 20 hours under stirring at 200 rpm. The pressure within the autoclave was 7.8 bar, and the pH was 13.4 at the beginning of the reaction. The autoclave was then cooled to 35° C., thus obtaining a suspension having a pH of 11.9. Per 1 kg of reactor content 168 g of diluted acid were added. About 80% of the calculated total amount of premixed nitric acid (10 wt.-% aqueous solution) was fed into the reactor under agitation. About 20% were slowly added in smaller portions until pH reached about 7-7.5. The resulting mixture was then filtrated with a filter press, and the filter cake was washed with deionized water to a conductivity of 200 microSiemens/cm. The wet product was heated to a temperature of 120° C. in air within 30 min and dried at that temperature for 4 hours. The dried product was then heated to a temperature of 600° C. within 4 hours and calcined in air at 600° C. for 5 hours to afford zeolite crystals having a CHA framework as observed by XRD.

For preparing the ammonium form of the calcined zeolite crystals an ammonium nitrate solution was prepared by mixing 55.6 g of 54 wt.-% ammonium nitrate with 530 g of deionized water at 80° C. 300 g of the calcined zeolitic material was then added to this solution. The ion-exchange reaction between the Na/H-form of the zeolitic material and the ammonium ions was carried out by agitating the slurry at 600° C. for 1 hour. The pH was between 2.7 and 2.4 during the reaction. The resulting mixture was then filtered, washed until the filtrate had a conductivity of <200 microSiemens/cm, and the washed sample finally air dried.

The Si:Al molar ratio of the Chabazite seed crystals amounted to 16.7 as measured by inductively coupled plasma (ICP).

Figure 1:
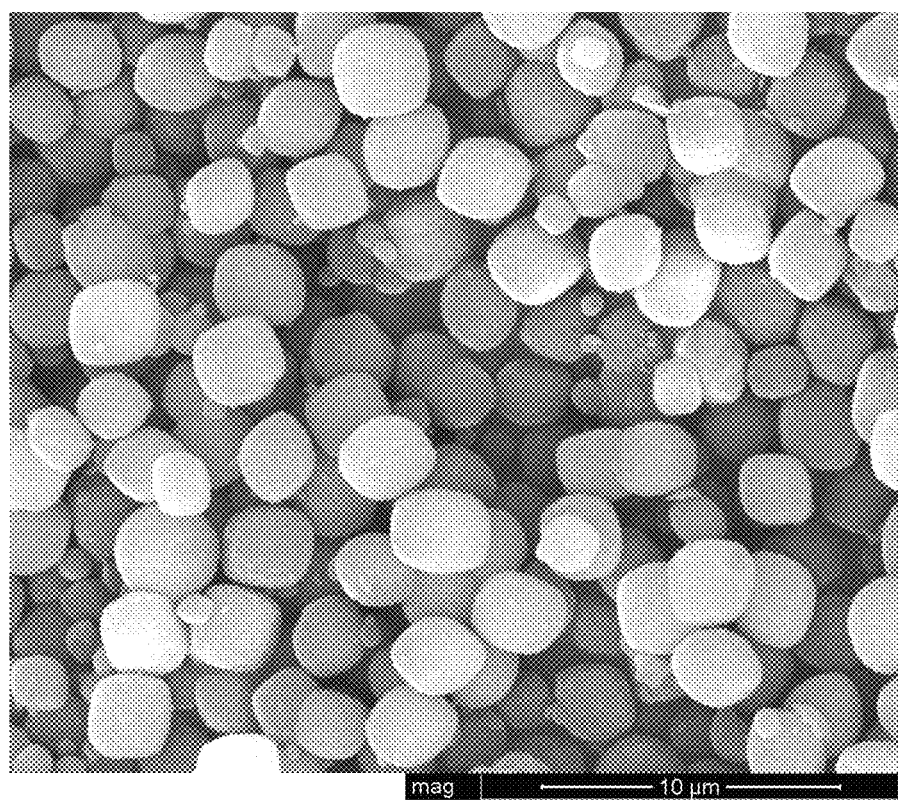
FIGS. 1A and 1B show images as obtained from scanning electron microscopy (SEM) conducted on the Chabazite seed crystals of Example 1.
Figure 1:
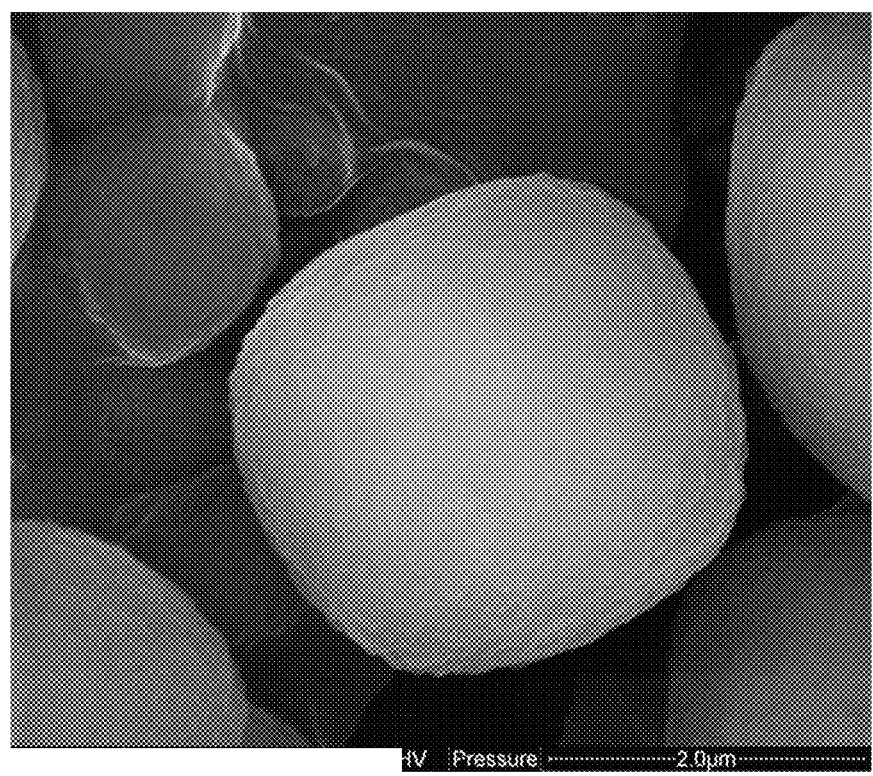

Images of the zeolite crystals as obtained from scanning electron microscopy (SEM) at two different magnifications are displayed in FIGS. 1A and 1B. In particular, as may be taken from the SEM images, the Chabazite seed crystals display the specific characteristics for seed crystals as defined in the present invention, in particular with respect to their diameter.

Synthesis of a Chabazite/SAPO-34 Core-Shell Zeolite 2.914 g of Boehmite (Al$_2$O$_3$, 70 wt. %) were added into 14.696 g of H$_2$O. After stirring at room temperature for 1 h, 2.132 mL of H$_3$PO$_4$ were added. After stirring at room temperature for 1 h, 2.286 g of silica sol gel (31.5 wt %) were added, followed by addition of 4.14 mL of DEA (diethylamine) used as the organotemplate. After stirring at room temperature for 12 h, 0.2 g of the Chabazite seed crystals was added into the gel. After stirring at room temperature for 15 min, the gel was placed into an autoclave for crystallization at 200° C. for 12 h. After having let the reaction mixture cool to room temperature, the crystallization product was filtered off from the mother liquor and dried.

Example 2

2.914 g of Boehmite (Al$_2$O$_3$, 70 wt %) were added into 18.954 g of H$_2$O. After stirring at room temperature for 1 h, 4.612 g of H$_3$PO$_4$ were added. After stirring at room temperature for 1 h, 0.722 g of fumed silica was added, followed by addition of 5.228 g of morpholine used as the organotemplate. After stirring at room temperature for 12 h, 0.2 g of the Chabazite seed crystals from Example 1 was added into the gel. After stirring at room temperature for 15 min, the gel was placed into an autoclave for crystallization at 200° C. for 12 h. After having let the reaction mixture cool to room temperature, the crystallization product was filtered off from the mother liquor and dried.

The BET-surface area of the crystalline product as measured on an ASAP 2020M system from Micromeritics amounted to 578 m²/g.

The synthetic procedure was repeated several times, wherein the reaction was respectively interrupted after 1, 2, 3, and 9 h.

Figure 2:
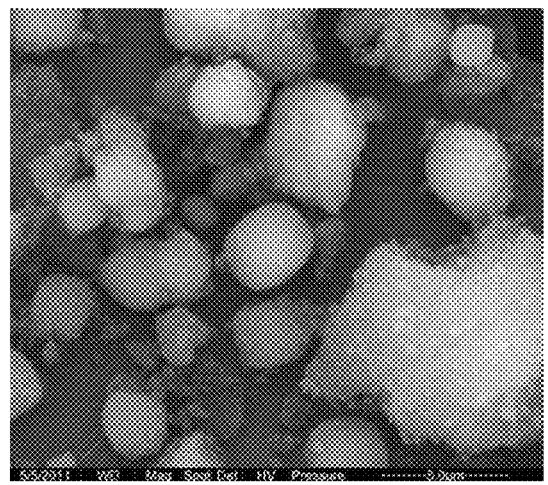
FIGS. 2A-2C show SEM images obtained from the crystallization product of Example 2 after 1, 2, and 9 hours of crystallization, respectively. In the respective SEM images, the scale indicated at the bottom right indicates a length of 5 μm in the SEM images obtained after 1 h and 2 h, and a length of 20 μm in the SEM image obtained after 9 h.
Figure 2:
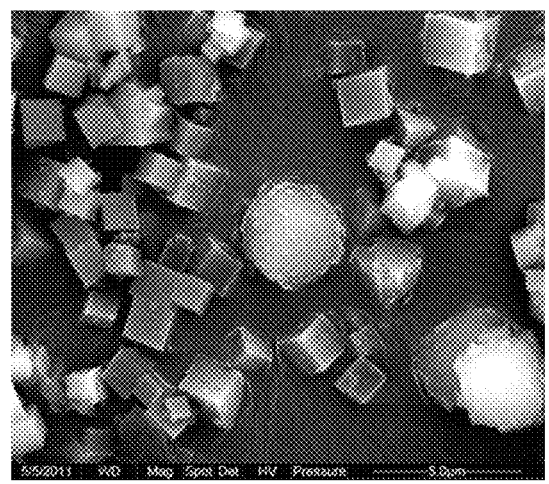
Figure 2:
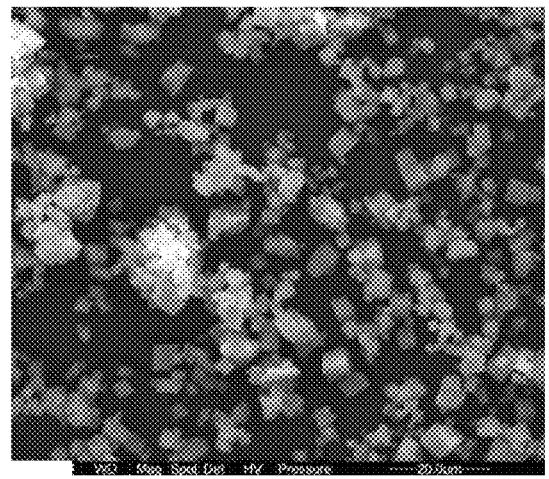
Figure 3:
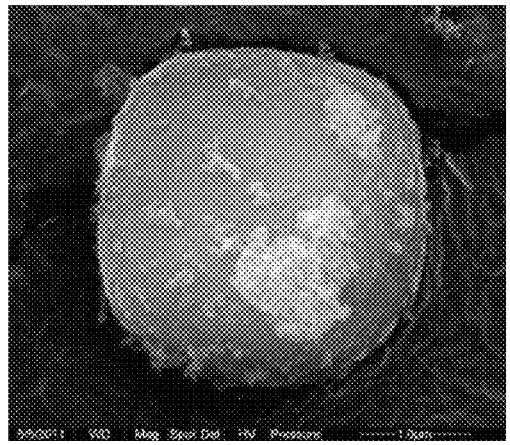
FIGS. 3A-3C show SEM images of a Chabazite seed crystals contained in the crystallization product of Example 2 after 1, 2, and 9 hours of crystallization, respectively. In the respective SEM images, the scale indicated at the bottom right indicates a length of 5 μm.
Figure 3:
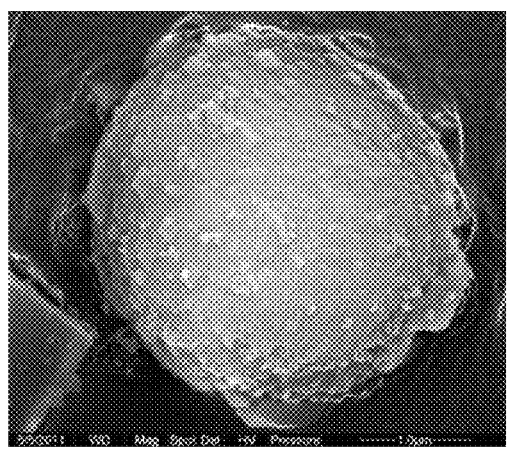
Figure 3:
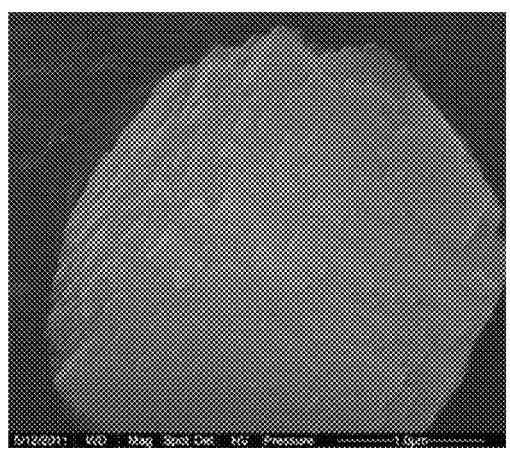
Figure 4:
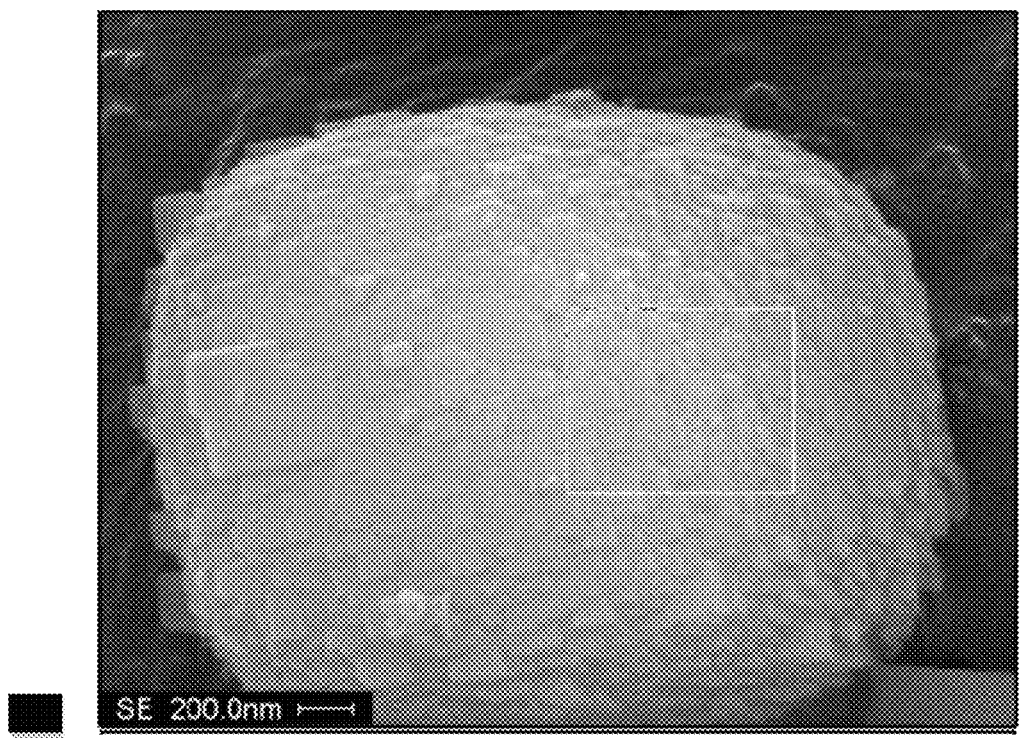
FIG. 4 shows an SEM image of a Chabazite seed crystal contained in the crystallization product of Example 2 after 3 hours of crystallization, wherein furthermore a white frame indicates the area of said crystal subject to energy dispersive X-ray spectroscopy (EDX). In the respective SEM image, the scale indicated at the bottom right indicates a length of 200 nm.

In FIGS. 2A, 2B and 2C; FIGS. 3A, 3B and 3C, and; FIG. 4, the images of the crystallization product as obtained from scanning electron microscopy (SEM) are displayed for the respective samples obtained after interruption of the crystallization process after 1, 2, and 9 h, respectively. In particular, as may be taken from the SEM image in FIG. 2A after interruption of the crystallization after 1 hour, only the Chabazite seed crystals are apparent. After 2 hours, however, a large amount of SAPO-34 crystals have already crystallized (FIG. 2B). Furthermore, it is apparent that the Chabazite seed crystals are now already covered with a shell of SAPO-34. This may well be recognized for the SEM images displayed in FIGS. 3A-3C, wherein details of the respective crystallization products relative to the Chabazite seed crystals contained therein is shown. Thus, as may be taken from FIG. 3B, it is apparent from the SEM images that a SAPO-34 shell has already been formed on the Chabazite seed crystals after only 2 hours of crystallization, wherein after 9 hours crystallization time (FIG. 3C) it is even more apparent that the Chabazite seed crystals are completely covered by a shell of SAPO-34, thus forming a Chabazite/SAPO-34 zeolitic material comprising a Chabazite core-portion and a SAPO-34 shell-portion according to the present invention.

In FIG. 4, the SEM image of a Chabazite/SAPO-34 zeolitic material comprising a Chabazite core-portion and a SAPO-34 shell-portion according to the present invention obtained after 3 hours of crystallization is displayed, wherein the white frame contained in said image indicates a surface of the zeolitic material which was subject to energy dispersive X-ray spectroscopy (EDX). In particular, EDX analysis of said surface afforded a concentration of aluminum, silicon and phosphorous in weight-% and atomic-%, respectively, as shown in the following Table 1:

TABLE 1

Concentrations obtained from EDX analysis of the crystal sample in FIG. 4

| Element | wt.-% | at.-% |
|---------|-------|-------|
| Al | 12.31 | 12.96 |
| Si | 69.94 | 70.75 |
| P | 17.75 | 16.28 |

Thus, the SAPO-34 shell material formed on the Chabazite seed crystals displays a P:X molar ratio of 1.26.

Figure 5:
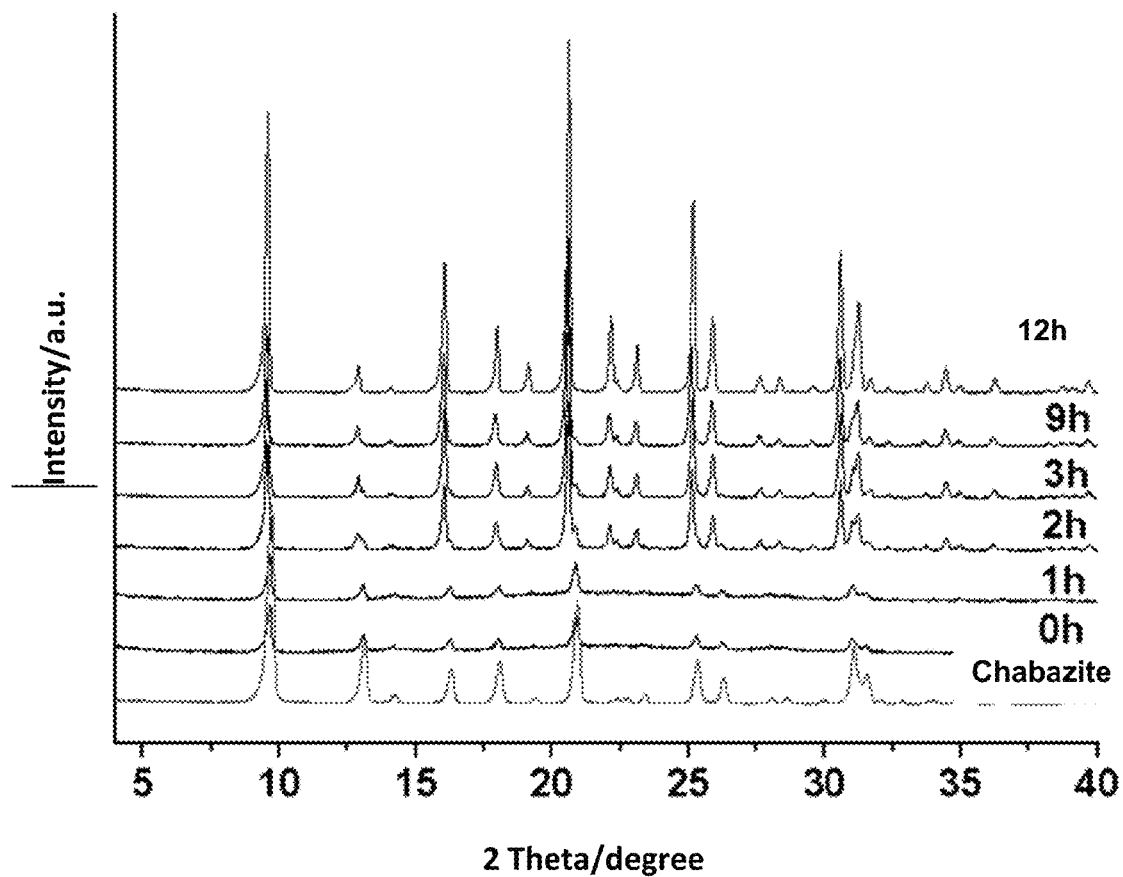
FIGS. 5 and 6 show the X-ray diffraction pattern of the crystalline material obtained for the Chabazite seed crystals of Example 1 (designated as "Chabazite"), as well as the X-ray diffraction patterns for the materials contained in the reaction product of Example 2 after 0 h of synthesis (synthesis mixture, designated as "0 h"), as well as after a crystallization period of 1 hour, 2 hours, 3 hours, 9 hours, and 12 hours (respectively designated as "1 h", "2 h", "3 h", "9 h" and "12 h"). In the respective figures, the angle 2 theta in ° is shown along the abscissa and the intensities are plotted along the ordinate.
Figure 6:
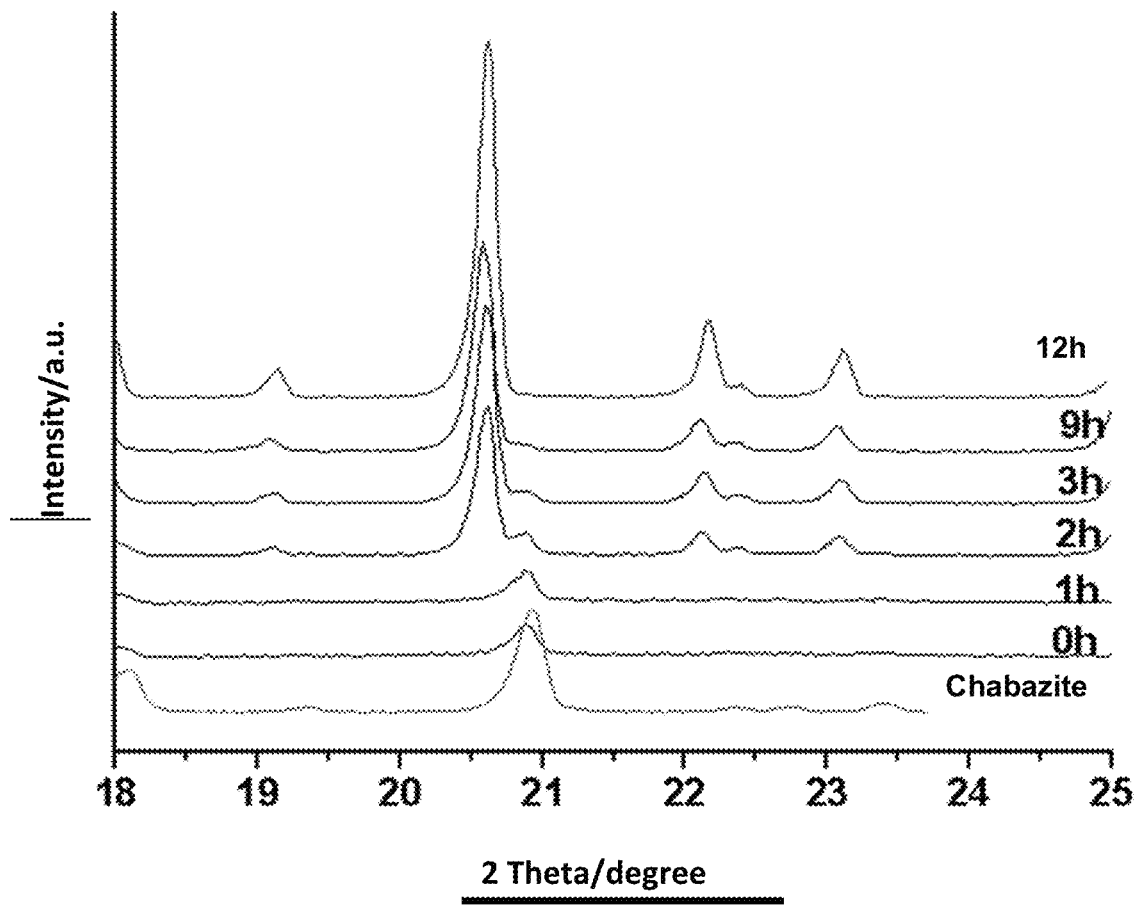

In FIGS. 5 and 6, the XRD pattern obtained for the Chabazite seed crystals is compared to the XRD patterns of the reaction mixture prior to crystallization (0h) as well as after 1, 2, 3, 9, and 12 h of crystallization, respectively. Thus, as discussed in the foregoing with respect to the SEM images in FIGS. 2A-2C and 3A-3C, it may also be taken from the XRD patterns of the samples that a notable amount of SAPO-34 is formed after just 2 hours of crystallization. Furthermore, as may be taken from FIG. 6 in which an enlarged portion of the XRD from FIG. 5 is shown, reflections from the Chabazite seed crystals used in synthesis are still clearly apparent in the XRD patterns after 2, 3, 9 and 12 h of crystallization, indicating that they are still present in the reaction product, the decreasing intensity of their reflections stemming from the increasing portion of SAPO-34 produced rather than from their eventual dissolution during the course of crystallization. This confirms the information obtained from the SEM images of the respective samples (see FIGS. 2A-2C, 3A-3C, and 4), wherein the seed crystals are rapidly covered by a layer of SAPO-34, thus forming the Chabazite/SAPO-34 zeolitic material comprising a Chabazite core-portion and a SAPO-34 shell-portion according to the present invention.

Accordingly, as has been shown by the SEM images and XRD patterns of the respective samples obtained after 2, 3, 9, and 12 h of crystallization under the conditions described above, by using specific Chabazite seed crystals according to the present invention, in particular relative to the diameter of the seed crystals, a notable amount of SAPO-34 may be crystallized after only a very short time of crystallization, such as for example after only 2 hours. Furthermore, the characteristics of the Chabazite seed crystals in particular with respect to their dimensions are such that they are not dissolved in the course of the crystallization process, but are rather covered by a shell of SAPO-34, thus affording a novel Chabazite/SAPO-34 zeolitic material comprising a Chabazite core-portion and a SAPO-34 shell-portion according to the present invention.

Example 3

Methanol to Olefin (MTO) Testing

Synthesis of SAPO-34 Without Seeding 2.914 g of Boehmite ($Al_2O_3$, 70 wt %) were added into 18.954 g of $H_2O$. After stirring at room temperature for 1 h, 4.612 g of $H_3PO_4$ were added. After stirring at room temperature for 1 h, 0.722 g of fumed silica was added, followed by addition of 5.228 g of Mor (Morpholine) template. After stirring at room temperature for 12 h, the gel was placed into an autoclave for crystallization at 200° C. for 48 h. After having let the reaction mixture cool to room temperature, the crystallization product was filtered off from the mother liquor and dried.

The BET-surface area of the crystalline product as measured on an ASAP 2020M system from Micromeritics amounted to 604 m²/g.

Catalyst Testing

MTO reactions were carried out at 400° C. in a flow-type fixed-bed micro-reactor under atmospheric pressure. For the catalyst testing, 0.5 g of a catalyst sample as obtained from Example 2 was used in the MTO reaction, wherein the weight hourly space velocity (WHSV) for methanol was set to 1.0 $h^{-1}$. As a comparative example, a physical mixture of SAPO-34 with the Chabazite crystals as obtained from Example 1 was used. The products of the MTO reaction were analyzed by an on-line gas chromatograph using a 50 m HP-PONA methylsiloxane capillary column and a flame ionization detector (FID).

The results from MTO catalyst testing are respectively displayed in FIGS. 7 and 8. In particular, upon comparing the results obtained using the zeolitic material of the present invention having a core-shell structure to those using a physical mixture of the Chabazite seed crystals with SAPO-34 it becomes apparent that the zeolitic material having a core-shell structure affords a higher selectivity that the comparative sample containing the physical mixture, in particular with respect to $C_3$-olefins. More interestingly, however, the inventive sample displays a tremendous increase in the catalyst lifetime compared to the physical mixture of SAPO-34 and Chabazite. In this respect, may be noted that the lifetime of a catalyst methanol to olefin synthesis, and in particular of Chabazite which may be used therein, is often limited due to coke formation on the catalyst. This is due to the comparatively strong acid sites of the Chabazite zeolite. As a result of this, the catalyst requires frequent regeneration or renewal.

By using a zeolitic material according to the present invention having a core-shell structure with a Chabazite core-portion and a SAPO-34 shell-portion, coke formation may effectively be suppressed due to the weaker acidity of SAPO-34 located on the outside of the core-shell structure. As a result, the typical coke formation observed when using Chabazite may be significantly reduced without, however, notably reducing the high activity of Chabazite in the methanol to olefin reaction. Accordingly, a considerably improved MTO catalyst is provided due to the core-shell structure of the inventive zeolitic material having a CHA framework structure.

CITED PRIOR ART DOCUMENTS

U.S. Pat. No. 7,067,108 B2
U.S. Pat. No. 6,974,889 B1

The invention claimed is:

1. A process for the preparation of a zeolitic material having a CHA framework structure, said zeolitic material comprising zeolite crystals having a core-shell structure, wherein said process comprises the steps of
(1) providing a mixture comprising one or more sources for $Z_2O_5$, one or more sources for $X_2O_3$, optionally one or more structure directing agents, and seed crystals having a CHA framework structure, wherein the CHA framework structure of the seed crystals comprises $YO_2$, $X_2O_3$, and wherein the seed crystals have a diameter of 450 nm or greater; and
(2) crystallizing the mixture provided in (1) to afford zeolite crystals comprising a core of seed crystal provided in step (1) and a shell crystallized on the seed crystal;
wherein Z is a pentavalent element, Y is a tetravalent element, and X is a trivalent element,
wherein the framework structure of the seed crystals does not comprise $Z_2O_5$ in addition to $X_2O_3$ and $YO_2$.

2. The process of claim 1, wherein the seed crystals have a diameter comprised in the range of from 450 nm to 50 μm.

3. The process according to claim 1, wherein the CHA framework structure of the seed crystals displays a Y:X molar ratio comprised in the range of from 1 to 100.

4. The process according to claim 1, wherein one or more sources for $YO_2$ are further provided in step (1), wherein Y comprised in the seed crystals
and/or,
wherein Y further provided in step (1) in the one or more sources for $YO_2$ are, independently from one another, selected from the group consisting of Si, Sn, Ti, Zr, Ge, and combinations of two or more thereof.

5. The process according to claim 1, wherein X comprised in the seed crystals
and/or,
wherein X provided in step (1) in the one or more sources for $X_2O_3$ are, independently from one another, selected from the group consisting of Al, B, In, Ga, and combinations of two or more thereof.

6. The process according to claim 1,
wherein Z provided in step (1) in the one or more sources for $Z_2O_5$ are, independently from one another, selected from the group consisting of P, As, Sb, Bi, V, Nb, Ta, and combinations of two or more thereof.

7. The process according to claim 1, wherein the seed crystals comprise one or more zeolites selected from the group consisting of (Ni(deta)$_2$)-UT-6, Chabazite, |Li-Na| [Al—Si—O]-CHA, DAF-5, Dehyd. Na-Chabazite, K-Chabazite (Iran), LZ-218, Linde D, Linde R, MeAPSO-47, Phi, SAPO-34, SAPO-47, SSZ-13, SSZ-62, UiO-21, Willhendersonite, ZK-14, ZYT-6, and combinations of two or more thereof.

8. The process according to claim 1, wherein the one or more sources for $Z_2O_5$ comprises one or more phosphates and/or one or more oxides and/or one or more acids of phosphorous.

9. The process according to claim 1, wherein the one or more sources for $X_2O_3$ comprises one or more compounds selected from the group consisting of aluminate salts, aluminum hydroxides, aluminum oxide hydroxides, and mixtures of two or more thereof.

10. The process according to claim 1, wherein one or more sources of $YO_2$ are provided in step (1), wherein the one or more sources for $YO_2$ comprises one or more compounds selected from the group consisting of silicas, silicates, and mixtures of two or more thereof.

11. The process according to claim 1, wherein the $X_2O_3$:$Z_2O_5$ molar ratio of the one or more sources of $X_2O_3$ and of the one or more sources of $Z_2O_5$ of the mixture provided in step (1) is comprised in the range of 1:(0.05-30), and
wherein if the mixture provided in step (1) further comprises $YO_2$, the $YO_2$:$X_2O_3$:$Z_2O_5$ molar ratio of the mixture provided in step (1) is comprised in the range of (0.01-10):1:(0.05-30).

12. The process according to claim 1, wherein the amount of seed crystals in the mixture provided in step (1) ranges from 1-90 wt.-% based on 100 wt.-% of the total amount of $X_2O_3$, $Z_2O_5$, and optional $YO_2$ respectively comprised in the one or more sources for $X_2O_3$, $Z_2O_5$.

13. The process according to claim 1, wherein the mixture provided in step (1) further comprises a solvent.

14. The process according to claim 13, wherein the solvent comprises water, wherein the $H_2O$:$Z_2O_5$ molar ratio of the mixture according to step (1) ranges from 5-100,
and/or,
wherein the $H_2O$:$X_2O_3$ molar ratio of the mixture according to step (1) ranges from 5-150.

15. The process according to claim 1, wherein the crystallization in step (2) involves heating of the mixture.

16. The process according to claim 15, wherein the heating in step (2) is conducted under autogenous pressure.

17. The process according to claim 15, wherein the crystallization in step (2) involves the heating of the mixture for a period ranging from 1 to 50 h.

18. The process according to claim 1, wherein the structure directing agent comprises one or more compounds selected from the group consisting of tetraalkylammonium compounds, dialkyl amines, heterocyclic amines, and combinations of two or more thereof.

19. The process according to claim 1, wherein the zeolitic material having a CHA framework structure crystallized in step (2) comprises one or more zeolites selected from the group consisting of [Al—As—O]-CHA, [Al—Co—P—O]-CHA, [Co—Al—P—O]-CHA, [Mg—Al—P—O]-CHA, [Zn—Al—P—O]-CHA, AlPO-34, CoAPO-44, CoAPO-47, GaPO-34, MeAPO-47, MeAPSO-47, SAPO-34, SAPO-47, ZYT-6, and combinations of two or more thereof.

20. A zeolitic material having a CHA framework structure obtained according to the process of claim 1.

21. A zeolitic material having a CHA framework structure, said zeolitic material comprising zeolite crystals having a core-shell structure, wherein the core-portion of the zeolite crystals comprises $YO_2$, $X_2O_3$, and optionally $Z_2O_5$ in the zeolite framework structure of said core-portion, and wherein the shell-portion of the zeolite crystals comprises $Z_2O_5$ and $X_2O_3$ in the zeolite framework structure of said shell-portion, wherein Y is a tetravalent element, X is a trivalent element, and Z is a pentavalent element, and wherein the core-portion displays a diameter of 450 nm or greater, wherein the Z:X molar ratio of the zeolite framework structure of the shell-portion of the zeolite crystals is greater than the Z:X molar ratio of the zeolite framework structure of the core-portion of the zeolite crystals by a factor of 1.5 or more.

22. The zeolitic material of claim 21, wherein the core-portion displays a diameter comprised in the range of from 450 nm to 50 μm.

23. The zeolitic material of claim 21, wherein the Z:X molar ratio of the zeolite framework structure of the shell-portion of the zeolite crystals is comprised in the range of from 0.01 to 20.

24. The zeolitic material of claim 21, wherein the Y:X molar ratio of the zeolite framework structure of the core-portion of the zeolite crystals is comprised in the range of from 1 to 100, and wherein if the zeolite framework structure of the core-portion of the zeolite crystals further comprises $Z_2O_5$ in addition to $YO_2$ and $X_2O_3$, the zeolite framework structure of the core-portion displays a Y:nX:pZ molar ratio, wherein the value for the ratio (1+2p):(n−p) is comprised in the range of from 1 to 100.

25. The zeolitic material of claim 21, wherein the shell-portion further comprises $YO_2$ in the zeolite framework structure of said shell-portion, and wherein Y comprised in the core-portion of the zeolite crystals and, Y comprised in the shell-portion of the zeolite crystals are independently selected from the group consisting of Si, Sn, Ti, Zr, Ge, and combinations of two or more thereof.

26. The zeolitic material of claim 21, wherein X comprised in the core-portion of the zeolite crystals and, X comprised in the shell-portion of the zeolite crystals are independently selected from the group consisting of Al, B, In, Ga, and combinations of two or more thereof.

27. The zeolitic material of claim 21, wherein Z comprised in the shell-portion of the zeolite crystals and Z, if present in the core-portion of the zeolite crystals, are independently selected from the group consisting of P, As, Sb, Bi, V, Nb, Ta, and combinations of two or more thereof.

28. The zeolitic material of claim 21, wherein the core-portion of the zeolite crystals comprises one or more zeolites selected from the group consisting of $(Ni(deta)_2)$-UT-6, Chabazite, |Li-Na| [Al—Si—O]-CHA, DAF-5, Dehyd. Na-Chabazite, K-Chabazite (Iran), LZ-218, Linde D, Linde R, MeAPSO-47, Phi, SAPO-34, SAPO-47, SSZ-13, SSZ-62, UiO-21, Willhendersonite, ZK-14, ZYT-6, and combinations of two or more thereof.

29. The zeolitic material of claim 21, wherein the shell-portion of the zeolite crystals comprises one or more zeolites selected from the group consisting of [Al—As—O]-CHA, [Al—Co—P—O]-CHA, [Co—Al—P—O]-CHA, [Mg—Al—P—O]-CHA, [Zn—Al—P—O]-CHA, AlPO-34, CoAPO-44, CoAPO-47, GaPO-34, MeAPO-47, MeAPSO-47, SAPO-34, SAPO-47, ZYT-6, and combinations of two or more thereof.

30. The zeolitic material of claim 21, wherein the BET surface area of the zeolitic material determined according to DIN 66135 ranges from 250 to 750 $m^2/g$.

31. A method for ion-exchange comprising using a zeolitic material having a CHA framework structure according to claim 21 as a molecular sieve, or as an adsorbent.

32. A method for catalysis comprising using a zeolitic material having a CHA framework structure according to claim 21 as a catalyst and/or as a catalyst support.

* * * * *